(12) United States Patent
Blurton et al.

(10) Patent No.: US 11,026,670 B2
(45) Date of Patent: Jun. 8, 2021

(54) SYSTEM FOR ABSORBING SWEAT FROM WITHIN A SKINFOLD OF A PATIENT

(71) Applicant: Stetrix, Inc., Oakland, TN (US)

(72) Inventors: David D. Blurton, Whiteville, TN (US); Mark Buchanan, Atoka, TN (US)

(73) Assignee: Stetrix, Inc., Bartlett, TN (US)

( * ) Notice: Subject to any disclaimer, the term of this patent is extended or adjusted under 35 U.S.C. 154(b) by 0 days.

(21) Appl. No.: 17/000,662

(22) Filed: Aug. 24, 2020

(65) Prior Publication Data

US 2020/0383676 A1 Dec. 10, 2020

Related U.S. Application Data

(63) Continuation of application No. 16/579,603, filed on Sep. 23, 2019, now Pat. No. 10,751,038.

(60) Provisional application No. 62/735,429, filed on Sep. 24, 2018.

(51) Int. Cl.
| | |
|---|---|
| *A61B 17/02* | (2006.01) |
| *A61F 13/15* | (2006.01) |
| *A61B 17/00* | (2006.01) |
| *A61F 13/84* | (2006.01) |

(52) U.S. Cl.
CPC ........ *A61B 17/0218* (2013.01); *A61F 13/15* (2013.01); *A61B 2017/00544* (2013.01); *A61B 2017/00889* (2013.01); *A61B 2017/0212* (2013.01); *A61B 2017/0225* (2013.01); *A61B 2218/007* (2013.01); *A61F 2013/15008* (2013.01); *A61F 2013/16* (2013.01); *A61F 2013/8414* (2013.01)

(58) Field of Classification Search
CPC ...... A61B 17/0218; A61B 2017/00544; A61B 2017/0889; A61B 2017/0212; A61B 2017/0225; A61B 2218/007; A61F 13/15; A61F 13/00042; A61F 13/00029; A61F 13/00046; A61F 13/00068; A61F 13/069; A61F 13/14; A61F 5/4404; A61F 2013/15008; A61F 2013/16; A61F 2013/8414; A61F 2013/00174; A61F 2013/00246; A61F 2013/00536; A61F 2013/00855; A47C 21/044; A47C 27/082; A47C 27/088; A47C 31/006; A61M 1/0001; A61G 2200/16
See application file for complete search history.

(56) References Cited

U.S. PATENT DOCUMENTS

| | | | |
|---|---|---|---|
| 5,678,564 | A | 10/1997 | Lawrence et al. |
| 6,168,612 | B1 | 1/2001 | Augustine et al. |
| 6,354,099 | B1 | 3/2002 | Bieberich |
| 6,519,964 | B2 | 2/2003 | Bieberich |

(Continued)

*Primary Examiner* — Pedro Philogene
(74) *Attorney, Agent, or Firm* — Haynes and Boone, LLP

(57) ABSTRACT

A tissue retraction system that allows aeration in a skinfold of a patient needing medical attention may include a flexible frame having a defined body shape comprising an internal facing surface configured to face a crease in the skinfold, an external facing surface opposite the internal facing surface configured to face outwardly and away from the patient, a first tissue facing surface, and a second tissue facing surface opposing the first tissue facing surface. Each of the first and the second tissue facing surfaces may be configured to engage against opposing sides of the skinfold.

27 Claims, 20 Drawing Sheets

(56) References Cited

U.S. PATENT DOCUMENTS

| | | | |
|---|---|---|---|
| 6,537,307 B1 | 3/2003 | Augustine et al. | |
| 6,718,785 B2 | 4/2004 | Bieberich | |
| 7,469,432 B2 | 12/2008 | Chambers | |
| 7,712,164 B2 | 5/2010 | Chambers | |
| 7,901,389 B2 * | 3/2011 | Mombrinie | A61M 1/008 604/317 |
| 8,287,508 B1 | 10/2012 | Sanchez | |
| 8,376,972 B2 | 2/2013 | Fleishmann | |
| 8,715,267 B2 * | 5/2014 | Bengtson | A61M 1/0088 604/541 |
| 9,044,368 B2 | 6/2015 | Fairburn | |
| 9,925,072 B2 | 3/2018 | Jonsson et al. | |
| 10,624,727 B2 | 4/2020 | Jonsson et al. | |
| 2008/0026023 A1 | 1/2008 | Tauer et al. | |
| 2009/0081926 A1 | 3/2009 | Gros | |
| 2011/0038919 A1 | 2/2011 | Tauer et al. | |
| 2012/0024296 A1 | 2/2012 | Long Sharps et al. | |
| 2012/0207811 A1 | 8/2012 | Tauer et al. | |
| 2012/0296293 A1 | 11/2012 | Clifford et al. | |
| 2013/0172802 A1 | 7/2013 | Cavanaugh et al. | |
| 2016/0317138 A1 | 11/2016 | Kasic, II | |
| 2016/0374848 A1 | 12/2016 | Sanchez et al. | |
| 2017/0143534 A1 | 5/2017 | Sanchez | |
| 2017/0266031 A1 * | 9/2017 | Sanchez | A61D 99/00 |
| 2017/0348139 A1 | 12/2017 | Newton et al. | |

* cited by examiner

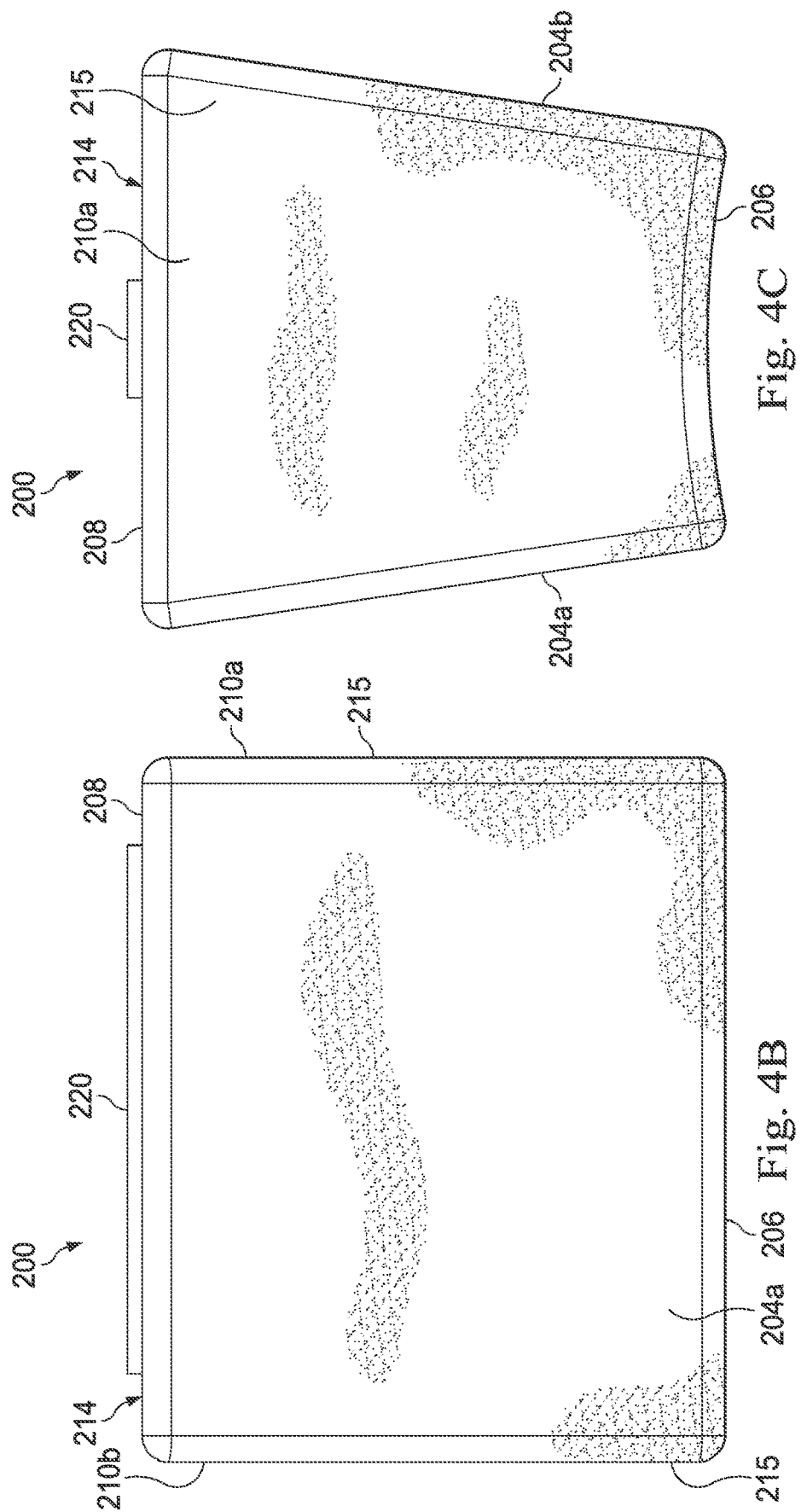

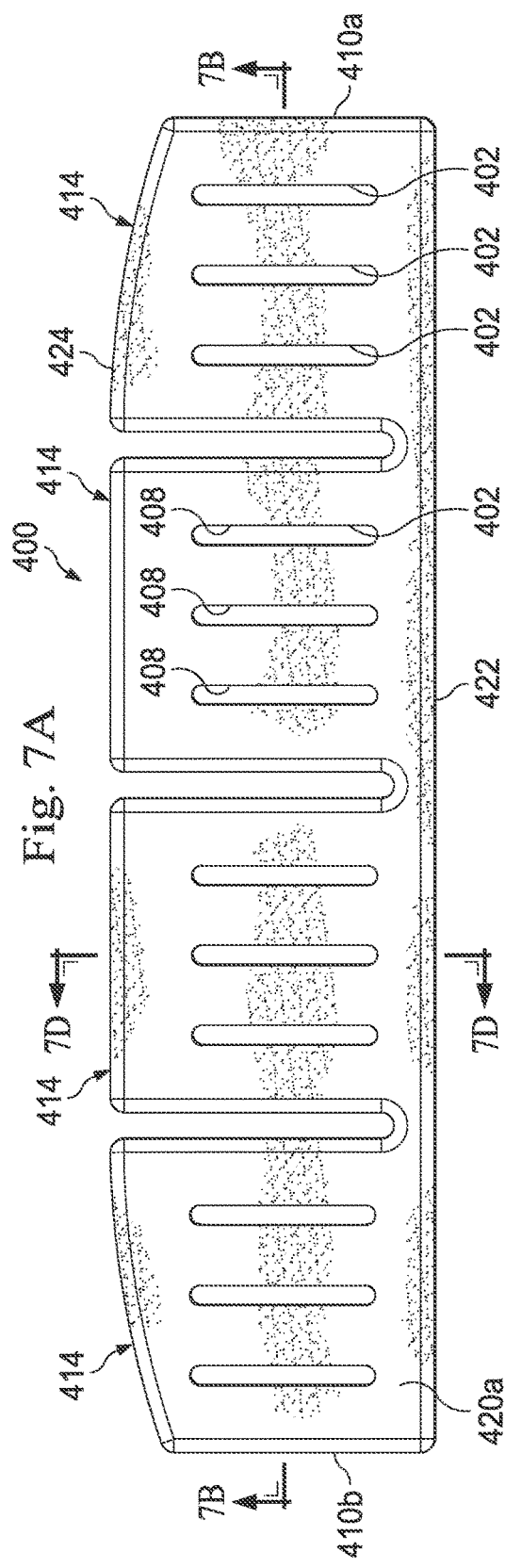
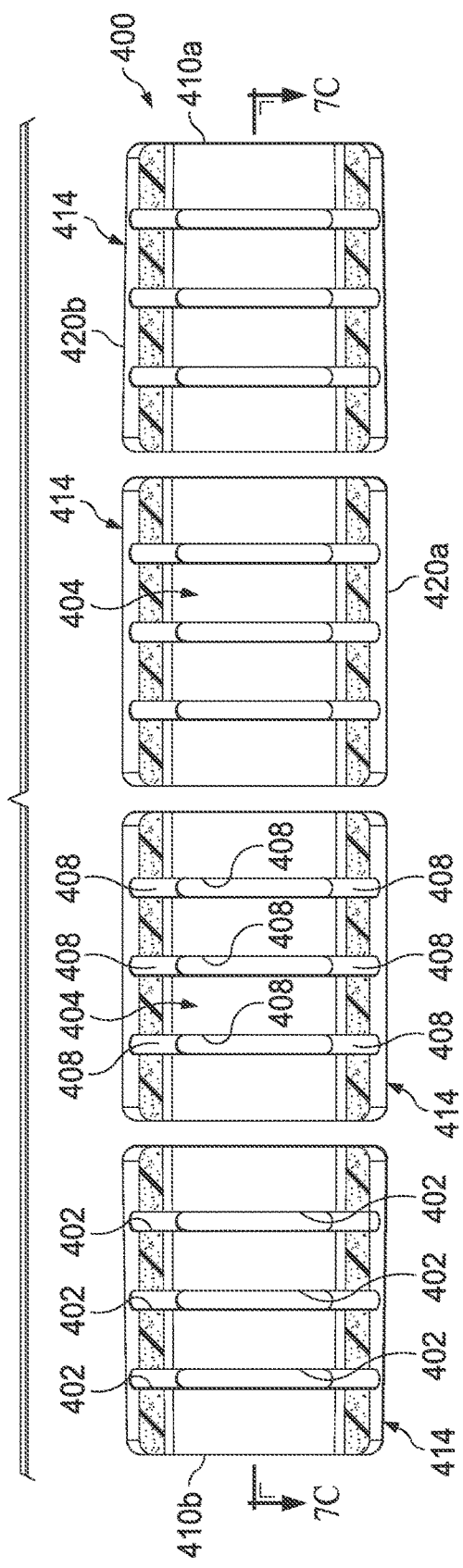
Fig. 7A
Fig. 7B

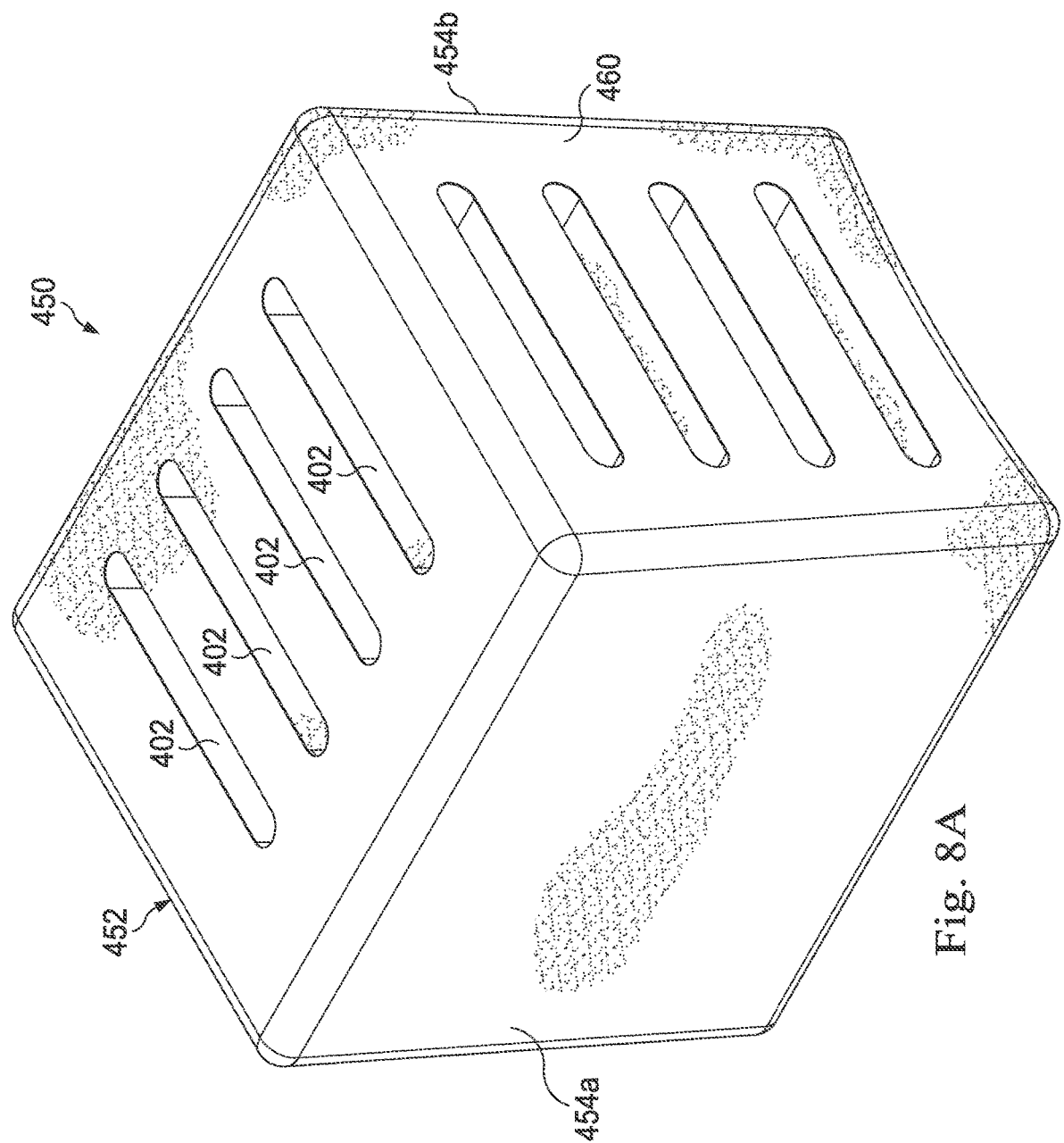

SYSTEM FOR ABSORBING SWEAT FROM WITHIN A SKINFOLD OF A PATIENT

PRIORITY INFORMATION

This application is a continuation of U.S. application Ser. No. 16/579,603, filed Sep. 23, 2019, now U.S. Pat. No. 10,751,038, which claims the benefit of U.S. Provisional Patent Application No. 62/735,429, filed Sep. 24, 2018, each of which is incorporated herein by reference in its entirety.

TECHNICAL FIELD

This disclosure relates in general to systems and methods for retracting and aerating user's skin fold. More particularly, in some implementations, this disclosure relates to systems and methods for maintaining folds of adipose patient body tissue in a displaced position and/or for providing aeration within the folds of tissue, for example, during or after a medical procedure on a patient.

BACKGROUND

For some morbidly obese patients, there is a need to retract the abdominal panniculus during surgery. One example is when an obese patient needs to have a cesarean section performed for childbirth. In these instances, the abdominal panniculus frequently overlaps the location where the surgical incision needs to be made and thus, the skinfold must be retracted to allow access for the surgery to be performed.

Pannus retractors that retract the pannus for surgical intervention are known. Most employ the use of adhesive on the patients' skin. Non-adhesive pannus retractors for surgical applications employ straps or apparatuses that attach to the surgical table. A limitation of these types of devices is that they do not permit ambulatory mobility of the patient in a post-surgical environment (i.e. recovery, hospital room, or patient's home).

In addition to requiring panniculus retraction for surgical access, many morbidly obese patients require additional postsurgical attention. The incision site may lie between the folds of skin of the panniculus. The inside of this skin fold is frequently irritated or infected with intertrigo due to the moist environment and inability of perspiration to escape. Compromised skin integrity within the panniculus is not only uncomfortable for the patient, but also increases the chance of causing an infection.

Some examples of prior treatments include wicking materials inserted within the fold skin fold. A limitation of these types of products is that the inside of the skin fold remains damp, even while excess sweat is transported to material outside the skin fold for evaporation. Other attempts to eliminate intra-fold sweat within the pannus include the use of abdominal support binders or suspenders. Limitations of these examples of prior treatments include: using compression around the abdomen and incision site (post-surgical compression can be uncomfortable and increase the potential to sweat), incorporation of belts or extensions that go behind the neck or extend proximally over the breasts (potentially uncomfortable and interfering with breast feeding). Other attempts to decrease intra-fold sweat within the panniculus include employing vacuum through an air-permeable substrate in an effort to move moisture. A limitation of this type of device is the requirement of a device to transport moisture from the skin to a location away from the patient.

Accordingly, the above-mentioned conventional systems all have shortcomings that continue to make medical procedures and subsequent healing difficult. The present disclosure overcomes one or more shortcomings in the art.

SUMMARY

The methods and systems disclosed herein include a tissue retraction system that allows aeration in a skinfold of a patient needing medical attention. Different embodiments are disclosed. One embodiment includes a tissue retraction system that allows aeration in a skinfold of a patient needing medical attention may include a flexible frame having a defined body shape comprising an internal facing surface configured to face a crease in the skinfold, an external facing surface opposite the internal facing surface configured to face outwardly and away from the patient, a first tissue facing surface, and a second tissue facing surface opposing the first tissue facing surface. Each of the first and the second tissue facing surfaces may be configured to engage against opposing sides of the skinfold.

In some exemplary aspects, the present disclosure is directed to a tissue retraction system that allows aeration between adjacent tissue surfaces of a user. The system may comprise a frame having a defined body shape comprising an internal facing surface configured to face a crease in the skinfold and an external facing surface opposite the internal facing surface configured to face outwardly and away from the patient. The system may also comprise a first tissue facing surface, and a second tissue facing surface opposing the first tissue facing surface. Each of the first and the second tissue facing surfaces may be configured to engage against opposing sides of the skinfold. The internal facing surface may comprise at least one air-flow channel formed therein to provide aeration within the skinfold.

In some aspects, the frame comprises a material that is one of flexible or rigid. In some aspects, the frame is sized to fit within a skinfold free of external adhesives or fastening elements. In some aspects, the internal facing surface is a recessed surface. In some aspects, the tissue retraction system comprises a superabsorbent material. In some aspects, the frame comprises an attachment feature for attaching an absorbent material. In some aspects, the frame is rigid. In some aspects, the system may include a positive or a negative pressure air flow device in fluid communication with the frame and configured to create airflow through or along the frame. In some aspects, the tissue retraction system may include a removable, absorbent cover disposed about the frame and configured to absorb liquids in the skinfold. In some aspects, the tissue retraction system may include a plurality of channels formed in at least one of the internal facing surface, the first tissue facing surface, and the second tissue facing surface.

In other exemplary aspects, the present disclosure is directed to a tissue retraction system that allows aeration between adjacent tissue surfaces of a user. The system may comprise a wedge-shaped frame having a defined body shape comprising an internal facing surface configured to face a crease in the skinfold, an external facing surface opposite the internal facing surface configured to face outwardly and away from the patient, a first tissue facing surface, and a second tissue facing surface opposing the first tissue facing surface. Each of the first and the second tissue facing surfaces may be configured to engage against opposing sides of the skinfold. The external facing surface may have a width and the internal facing surface may have a width. The width of the external facing surface may be greater than the width of the internal facing surface.

In some aspects, the frame may comprise a material that is one of flexible or rigid.

In other exemplary aspects, the present disclosure is directed to a tissue retraction system that allows aeration between adjacent tissue surfaces of a user. The system may include a frame having a defined body shape comprising an internal facing surface configured to face a crease in the skinfold and an external facing surface opposite the internal facing surface configured to face outwardly and away from the patient. The frame may include a first tissue facing surface and a second tissue facing surface opposing the first tissue facing surface. Each of the first and the second tissue facing surfaces may be configured to engage against opposing sides of the skinfold. The frame may have airflow features that direct airflow into or out of the skinfold. In some aspects, the frame has a cross-section that is one of curvilinear or elliptical. In some aspects, the tissue retraction system has a perforated sleeve or outer shell comprised of a material that is one of absorbent or antimicrobial. In some aspects, the frame is thermally conductive and removes heat from the patient. In some aspects, the frame is comprised of material that is one of flexible or rigid. In some aspects, the tissue retraction system includes a plurality of channels formed in at least one of the internal facing surface, the first tissue facing surface, and the second tissue facing surface. In some aspects, said frame is of generally cylindrical shape having a substantially circular cross-section, with the frame having an internal cavity and an outer surface. The tissue facing surfaces, said internal facing surface, and the external facing surface may be defined by respective curved portions of the circumference of said frame. In some aspects, said airflow features may include a plurality of external channels formed into and axially along said outer surface of said frame. In some aspects, said channels may be open at the outer surface of said frame and do not extend into said cavity. In some aspects, said channels may extend over an arc around at least a portion of the circumference of said outer surface of said frame. In some aspects, said arc is less than 180° about the circumference of the outer surface and may be included in at least one portion of the outer surface of said frame that defines one or both of the first and second tissue facing surfaces or the internal facing surface. In some aspects, the tissue retraction system may include one or more holes extending through said outer surface of said frame and into said cavity. In some aspects, said one or more holes may be aligned with one or more of said channels. In some aspects, airflow features may include one or more holes extending through said outer surface of said frame and into said cavity.

In other exemplary aspects, the present disclosure is directed to a method of providing aeration between adjacent tissue surfaces defined by a skinfold of a patient. The method may include preparing a tissue retraction system having an airflow feature; separating the skinfold of said patient; and introducing said retraction system into said skinfold. In some aspects, the method may include applying a material that is one of absorbent or antimicrobial onto the tissue retraction system. In some aspects, the method may include adjusting the tissue retraction system to have a desired length. In some aspects, the method may include attaching an airflow generator system.

Additional embodiments and methods of use are contemplated herein.

Further objects, forms, implementations, aspects, features, benefits, and advantages of the present disclosure shall become apparent from the detailed drawings and descriptions provided herein.

BRIEF DESCRIPTION OF THE DRAWINGS

FIG. 4B is an illustration of a side view of the exemplary tissue retraction system of FIG. 4A according to an exemplary implementation.

FIG. 4C is an illustration of an end view of the exemplary tissue retraction system of FIG. 4A according to an exemplary implementation.

FIG. 7A is an illustration of a side view of yet another exemplary tissue retraction system according to an exemplary implementation of the present disclosure.

FIG. 7B is an illustration of a cross-sectional view of the exemplary tissue retraction system of FIG. 7A taken through lines 7B-7B according to an exemplary implementation.

FIG. 8A is an illustration of a perspective view of yet another exemplary tissue retraction system according to an exemplary implementation of the present disclosure.

DETAILED DESCRIPTION

Figure 1A:
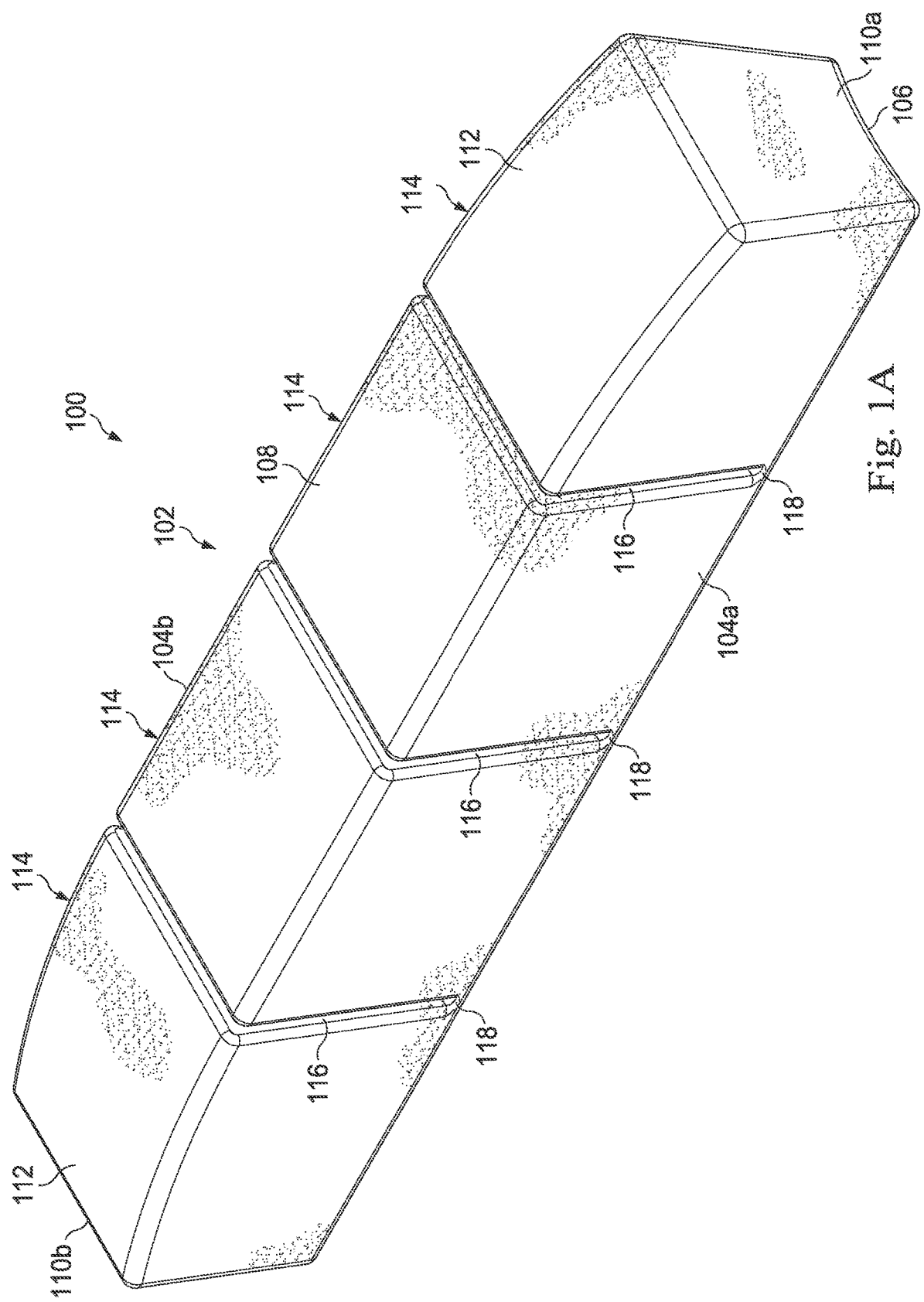
FIG. 1A is an illustration of a perspective view of an exemplary tissue retraction system according to an exemplary implementation of the present disclosure.

For the purposes of promoting an understanding of the principles of the invention, reference will now be made to certain implementations, or examples, illustrated in the drawings and specific language will be used to describe the same. It will nevertheless be understood that no limitation of the scope of the invention is thereby intended. Any alterations and further modifications in the described implementations, and any further applications of the principles of the invention as described herein are contemplated as would normally occur to one skilled in the art to which the invention relates.

Adipose tissue may hinder access to regions of the patient's body during routine or non-routine healthcare treatment. For example, in some instances, adipose tissue may detrimentally affect the ability to view or access regions of the patient's body to perform procedures, such as, for example, panniculectomies, to treat panniculitis, general wound care, femoral catheterization, tracheal intubation, cesarean sections, hysterectomies, among other medical procedures. Furthermore, when treatment occurs in areas within a fold of skin of the panniculus, the fold may have less than desirable access to fresh air, and may create a moist, bacteria rich environment in the area of the treatment due to the lack of access to fresh air.

The tissue retraction system disclosed herein includes an abdominal aeration device that may be used to maintain tissue or folds of skin in a retracted position that provides better healing potential to treatment areas underneath the folds of skin. For example, the tissue retraction system may be an abdominal aeration device that is structurally configured to separate skinfolds, and in some implementations, permit air to access the treatment site. In some implementations may abdominal aeration device may allow passive air access to the site. In some implementations, the abdominal aeration device may also include features that promote air movement. Air movement or airflow across the areas between folds of skin and/or a treatment site may help reduce the amount of perspiration that contributes to a moist environment between skinfolds.

While the emphasis of this disclosure is on separating folds of tissue of the pannus for healing of a mother after a cesarean section, it is noted that the present tissue retraction system has application in displacing or maintaining adipose tissue of other body regions for therapeutic applications, only some of which are discussed herein.

Turning now to FIGS. 1A, 1B, 1C, and 1D, the tissue retraction system, referenced herein by the numeral 100, includes a frame shaped and sized to fit within a crease or fold of a patient's pannus tissue. While the frame may comprise material that is flexible or rigid, since the shape and configuration are substantially identical, only the details of the various embodiments of the flexible frames are described herein for brevity. It is understood that the frames may also be rigid. The flexible frame 102 includes tissue facing surfaces 104a, 104b, an internal facing surface 106, and an external facing surface 108. As will be explained below, the tissue facing surfaces 104a, 104b are sized and shaped to fit between skinfolds of a patient and maintain the skin in a spaced-apart condition. In this example, the tissue facing surfaces 104a, 104b are nonparallel surfaces with the width 126 of the external facing surface 108 being greater than the width 124 of the internal surface 106, giving a wedge-shaped to the flexible frame 102. The wedge-shape may be more comfortable than a square or rectangular cross-section, although they and other cross-sectional shapes are contemplated herein. In some examples, the frame 102 may be formed with a square or rectangular cross-section, and circular or cylindrical cross-section or other shape. In some examples, the frame 102 may be formed with rounded or chamfered surfaces to provide additional comfort at contact corners that engage or contact patient tissue.

The internal facing surface 106 is shaped to fit adjacent the crease of the fold of tissue. In this embodiment, the internal facing surface 106 includes a concave shape that is configured to face the crease in the skinfold and that may space at least a part of the internal facing surface 106 from tissue of the body. In some implementations, the concave shape may allow a treated area, such as an incision site, to be left out of direct contact or engagement with the internal facing surface 106. Accordingly, the internal facing surface 106 may also allow some amount of air to be present adjacent the crease of the body fold. That is, air may be in contact with the intra-folded skin and may be exchanged. In some implementations, the internal facing surface 106 may have at least one air-flow channel formed therein to provide aeration through the flexible frame 102 within the skinfold. Although shown as concave, in other implementations, the internal facing surface 106 may be otherwise recessed without an arc-shape. In yet other implementations, the internal facing surface 106 may project outwardly to form a convex surface. Whether recessed, flat, or projecting, the internal facing surface 106 may comprise grooves, ridge, protruding dimples or may have other features that engage with only a portion of the intra-folded skin. Accordingly, air may still circulate between the internal facing surface 106 and the patient tissue, even though the internal facing surface may contact the patient tissue at one or more localized locations. This may still permit airflow against the patient tissue at the noncontact points.

The external facing surface 108 may be, in some implementations, wider than the internal facing surface 106. The external facing surface 108 is configured to face outwardly and away from the patient and may be spaced from the internal facing surface by a consistent distance or, as in the exemplary implementation shown, may taper at opposing ends 110a, 110b. The taper, referenced herein by the reference number 112, may be shaped to so that the flexible frame 102 remains substantially within a fold of the pannus. Since the depth of a fold of patient tissue may be less at the lateral sides of the patient's body than at the middle, the decreased height at the ends 110a, 110b may help keep the flexible frame 102 within the fold. In addition, the edges of the ends 110a, 110b may not project as far outside of the tissue fold. This may help reduce the likelihood of being bumped or inadvertently displaced as the patient moves around a hospital recovery room, at home, or other location where the patient may be using the tissue retraction system 100. The taper 112 may be seen in FIGS. 1B and 1C. In the implementation shown, the overall height of the frame 102 decreases toward each and 110a, 110b in FIG. 1C, this is shown in the interview where the frame 102 has a height 122, yet at the end 110a, the height is shown as smaller than height 102, referenced herein by the numeral 113. In some implementations, the overall height forms a taper that may be defined by a curve or may be defined by a straight slope. In some implementations, the taper is formed only along the external facing surface 108. In other implementations, the ends 110a, 110b may taper along multiple surfaces. In some implementations for example, the internal facing surface 106 and the external facing surface 108 also taper inwardly in the longitudinal direction. In yet other implementations, the internal facing surface 106 and the external facing surface 108 are substantially parallel along the longitudinal length of the frame 102.

In this implementation, the flexible frame 102 is formed of a plurality of support body segments 114. In this implementation, the support body segments 114 may be sufficiently rigid to maintain separation of a skin fold, yet flexible enough to comfortably be disposed within a fold of the patient. Here, the support body segments 114 are separated by one another by a cleft 116. Here, the cleft 116 extends substantially from the external facing surface 108 toward the internal facing surface 106, ending at a compliant joint 118. In this implementation, the compliant joint 118 may provide additional flexibility to the flexible frame 102 within a single plane. In addition, the clefts 116 may help the frame 102 conform to the radius of a pannus, and still allow the frame 102 to ship in a straight condition. In some implementations, the flexible frame 102 may be biased toward a straight condition and may be flexed by a healthcare provider when being introduced into a skinfold of a patient. In the implementation shown, the flexible frame 102 is generally elongated and substantially continuous. Because of the cleft 116, the support body segments 114 may extend from cleft to cleft and may include surfaces that define an edge or end 115 of the support body segments 114. In the implementation shown, each body segment 114 includes two ends 115. For the support body segment 114 that forms an end of the frame 102, one of the ends 115 is the same surface that forms the end 110a of the frame 102.

In some implementations, the compliant joints 118 also be a frangible joint that may permit relatively easy separation of one body segment 114 from another body segment 114 or from the frame 102. Accordingly, a user may tear the frame 102 to a desired length by removing one or more support body segments 114 from the frame 102. In yet other embodiments, the compliant joint 118 is not frangible, and may prevent separation of an adjacent support body segments 114. Furthermore, although described as being flexible in a single plane, in yet other embodiments, the compliant joint 118 may permit the frame 102 to be flexed in more than one plane.

Figure 1B:
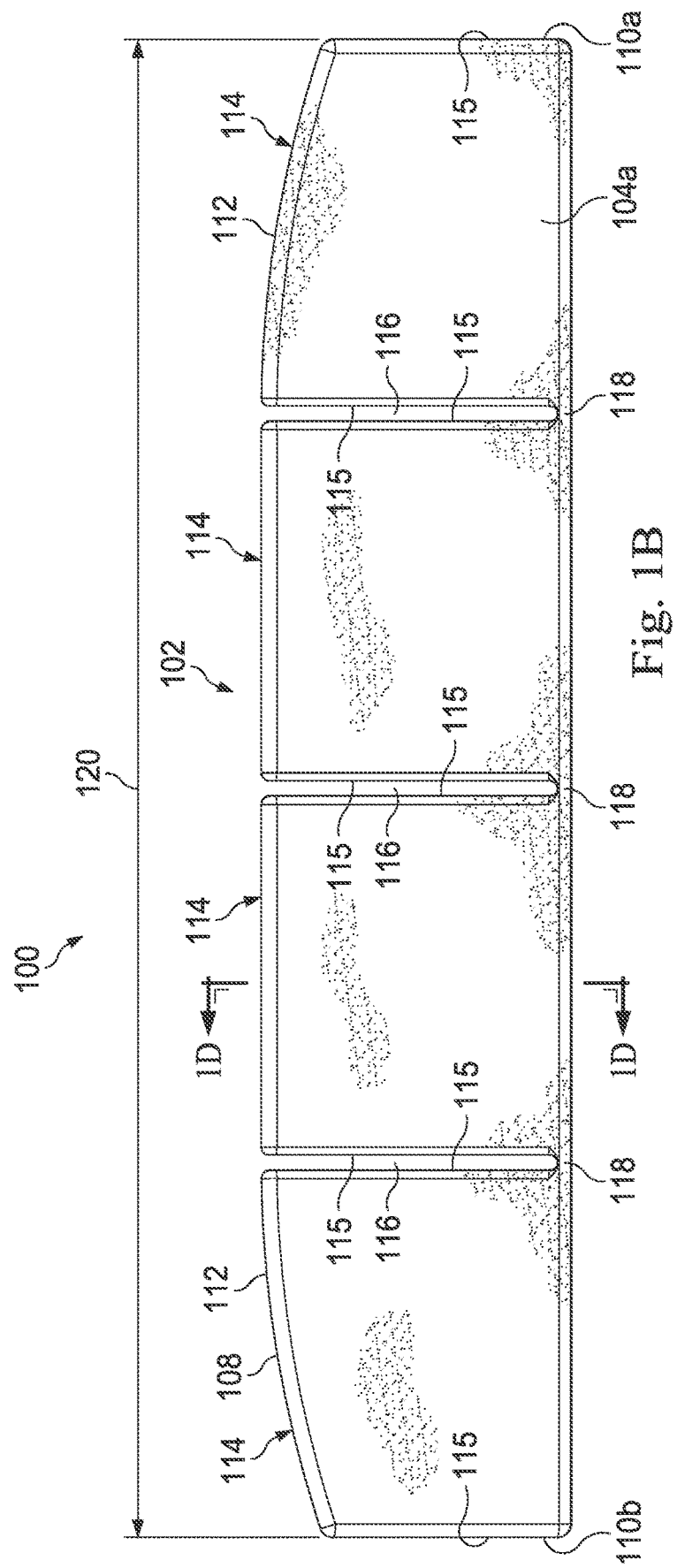
FIG. 1B is an illustration of a side view of the exemplary tissue retraction system according to an exemplary implementation.
Figure 1C:
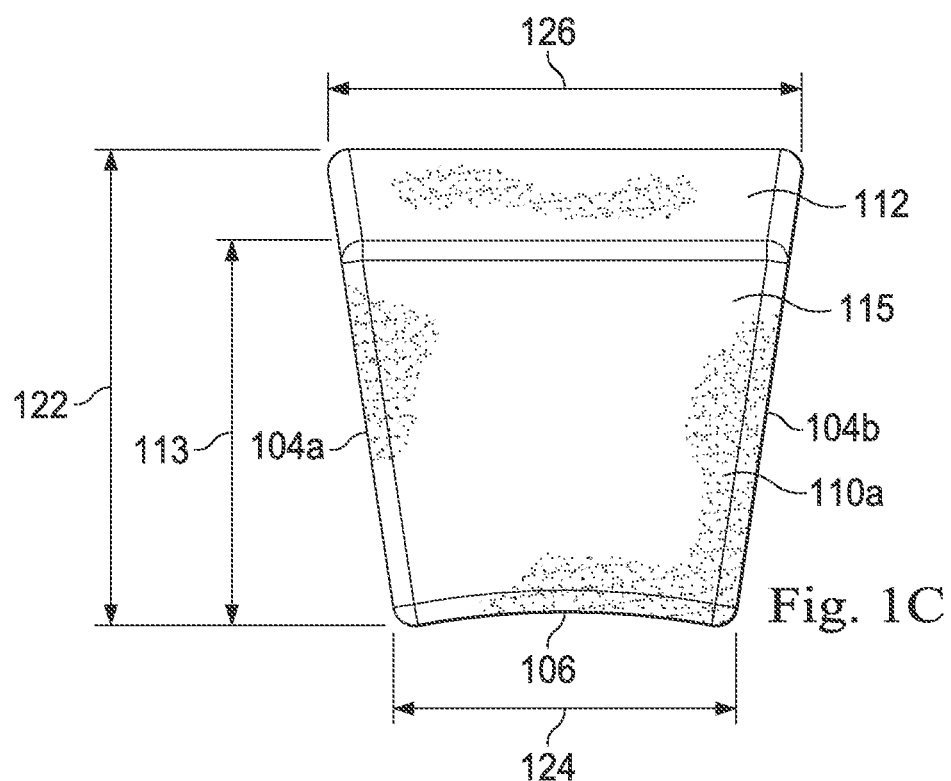
FIG. 1C is an illustration of an end view of the exemplary tissue retraction system according to an exemplary implementation.
Figure 1D:
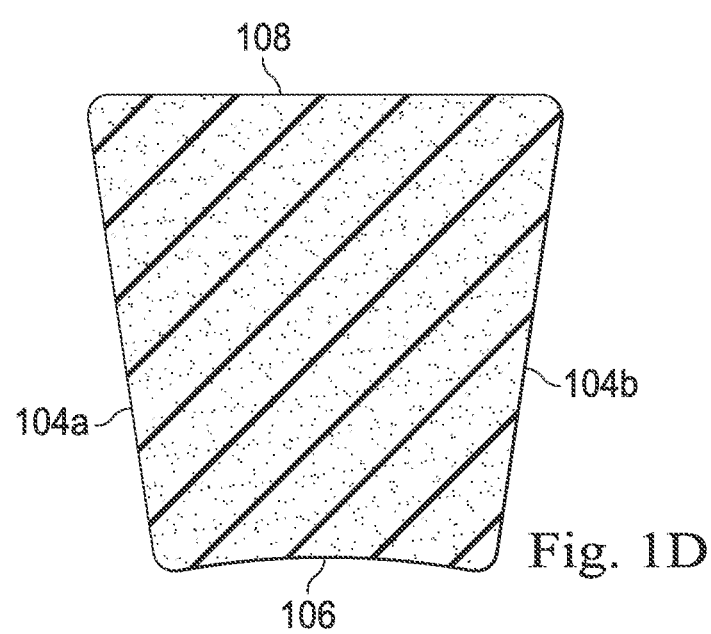
FIG. 1D is an illustration of a side cross-sectional view taken along lines 1D-1D in FIG. 1B of the exemplary tissue retraction system according to an exemplary implementation.

FIGS. 1B, 1C, and 1D show additional views of the tissue retraction system 100. The tissue retraction system 100 may be sized to fit between layers of skin of the patient, and some implementations may be particularly sized or customized to meet the size needs of individual patients. Accordingly, the size may vary, however some implementations of the flexible frame 102 may have a length within a range of about 6 to 60 inches. In some implementations, a length 120 may be within a range of about 6 to 36 inches, 12 to 36 inches, and 15 to 30 inches, although other ranges are contemplated. The height 122 may be in a range of about 3 to 8 inches, 4 to 7 inches, and 5 to 6 inches, although other ranges are contemplated. The width 124 of the internal facing surface 106 may be in a range of about 1.5 to 6 inches, 2 to 5 inches, 3 to 5 inches, although other ranges are contemplated. The width 126 of the external facing surface 108 may be in a range of about 2 to 10 inches, 3 to 8 inches, 4 to 7 inches, and 5 to 6 inches, although other ranges are contemplated.

The flexible frame 102 may be formed of any material sufficient to flexibly support the weight of the tissue, such as the pannus, including an open or a closed cell polyethylene, polyurethane, or other appropriate material. In some implementations, the flexible frame 102 is formed exclusively of superabsorbent material. For example, superabsorbent paper, cloth, or towels may form the flexible frame 102. In some embodiments, each support body segment 114 is formed to be somewhat flexible or compressible. This may provide additional comfort to the patient, particularly when the flexible frame 102 is disposed within a patient fold for an extended period of time. The flexible frame may be disposable or may be reusable. In some implementations, the flexible frame 102 or an absorbent material on the flexible frame 102 may be vapor permeable, perforated, or may contain voids that allow exposure of the skin to ambient air outside of the skinfold for increased evaporation of sweat. In addition, the material, shape, and design of the flexible frame 102 may help with dissipation of heat. This in turn may prevent sweat from occurring in the first place, helping maintain a healthier environment less conducive to bacteria growth. Some embodiments accommodate air exchange in a range of 2 cubic feet minute. In some embodiments, the outer surfaces of the flexible frame 102 are nonporous, while in other embodiments, the outer surfaces of the flexible frame are porous. Some implementations include microbial agents in the flexible frame 102 or other element of the tissue retraction system 100. For example, the tissue retraction system, including the flexible frame 102, may include copper, silver, or other antimicrobial substance therein. Some implementations of the frame 102 are thermally conductive. Accordingly, the frame may be utilized to remove heat from the patient when disposed between skinfolds. Thermally conductive materials may include metal materials, and may include thin-walled metal tubes, composites, nanotubes, and other thermally conductive materials.

As indicated previously, the internal facing surface 106 may be shaped to provide spacing between the internal facing surface 106 and the crease of the fold of the patient. In the embodiment disclosed, the internal facing surface 106 is concave. The depth of the concavity may be in a range of about 0.2 to 2 inches. In some implementations, the depth of the concavity may be in a range of about 0.2 to 1 inch. In the concave implementation, the concavity is arc shaped or otherwise shaped and may vary in order to provide a sufficient level of aeration. In yet other embodiments, a gap of some other shape or form provides the aeration. In some implementations, the internal facing surface 106 includes gaps, perforations, apertures or windows. In some implementations, the internal facing surface 106 is formed by struts or supports separated by apertures that promote air flow while maintaining sufficient rigidity between the tissue facing surfaces 104.

Figure 2A:
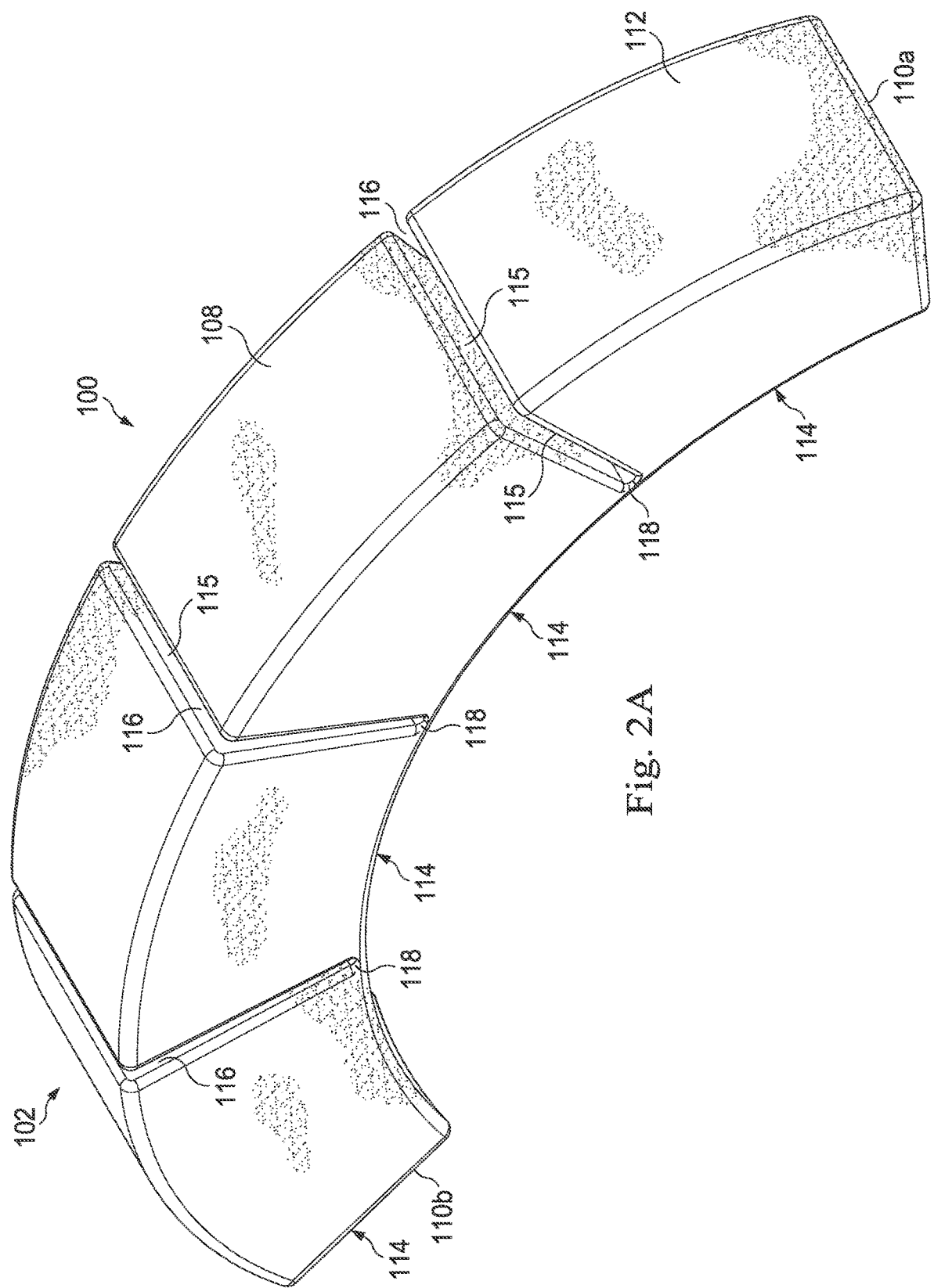
FIG. 2A is an illustration of a perspective view of the exemplary tissue retraction system in a flexed position according to an exemplary implementation of the present disclosure.
Figure 2B:
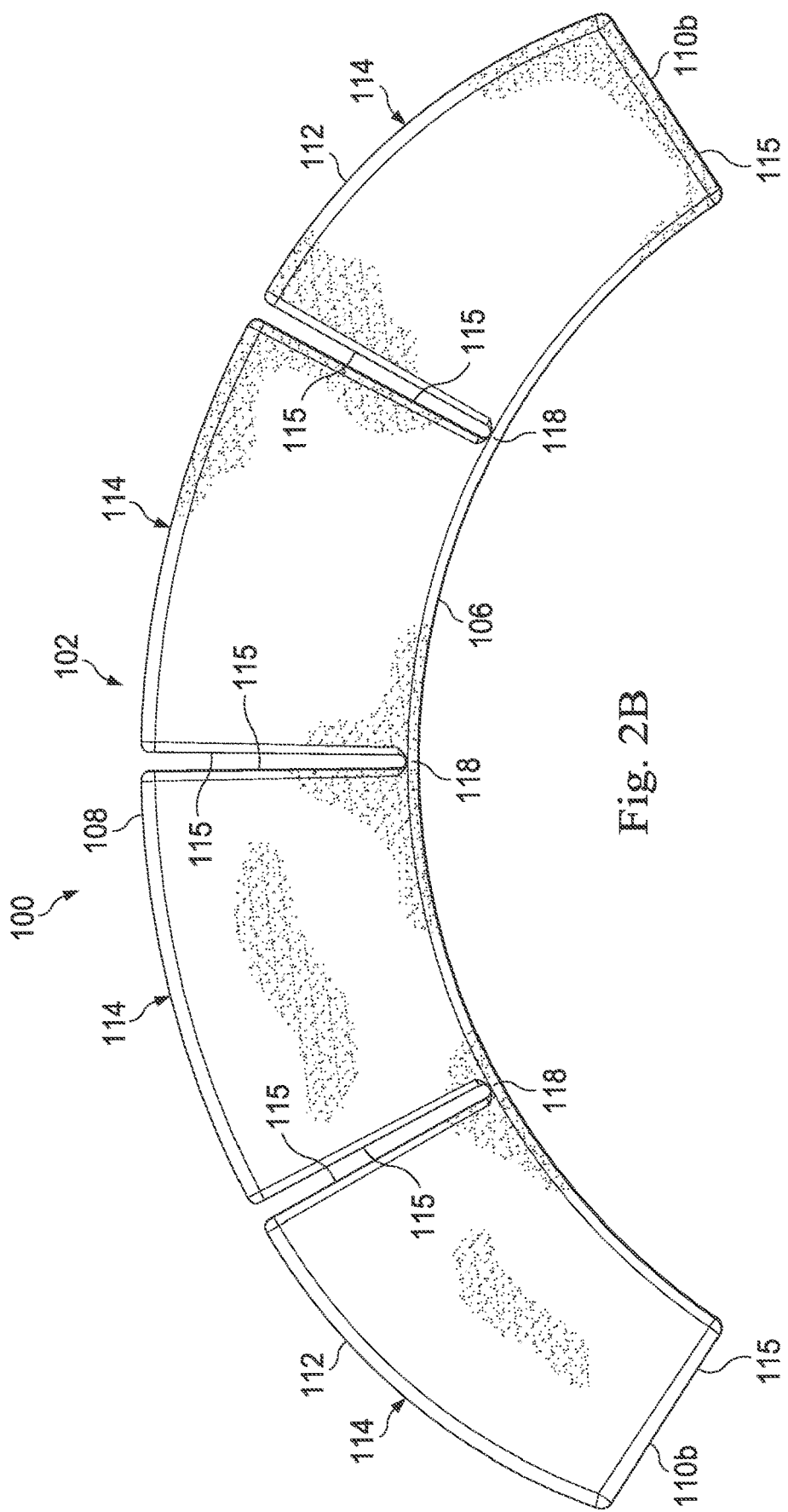
FIG. 2B is an illustration of a side view of the exemplary tissue retraction system in a flexed position according to an exemplary implementation of the present disclosure.

FIGS. 2A and 2B show the tissue retraction system 100 in a flexed condition. In this implementation, the support body segments 114 pivot relative to one another about compliant joint 118. This flexibility may assist the tissue retraction system 100 in conforming to a patient's body shape. As indicated above, the compliant joint 118 in this embodiment permits flexibility primarily in a single plane. In yet other embodiments, the compliant joint 118 may permit flexibility in more than a single plane.

Figure 3:
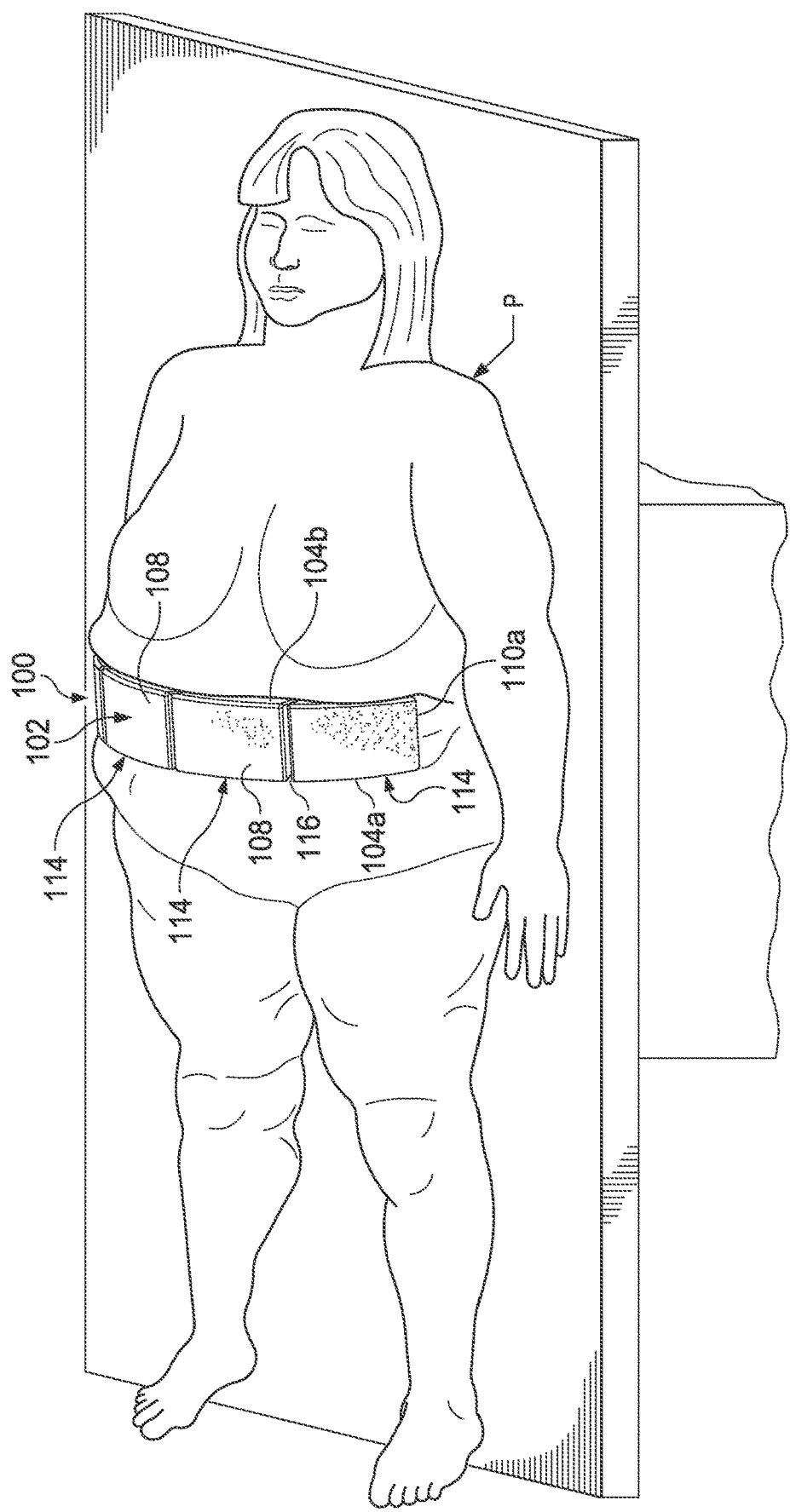
FIG. 3 is an illustration of a patient with the tissue retraction system disposed within a fold of adipose tissue according to an exemplary implementation of the present disclosure.

FIG. 3 shows the tissue retraction system disposed in a skin fold of the patient P. As can be seen, the flexible frame 102 is disposed within the pannus while maintaining separation of the skinfold. In this implementation, the tissue retraction system 100 is disposed in a fold of skin of the pannus. Accordingly, a first surface of the skin may abut against and be in contact with the tissue facing surface 104a, while an opposing surface of the skin may abut against and be in contact with the tissue facing surface 104b. Because of the shape and size of the tissue retraction system 100, the weight of an adjacent skin fold may be sufficient to hold the tissue retraction system in place. Accordingly, some implementations of the system 100 may be free of adhesives or appendages to keep the device in place. In some implementations, surface features may be used to increase frictional resistance of the skin and tissue facing surfaces so that the tissue retraction system 100 may be maintained within a skinfold without any other mechanical attachment mechanisms, such as adhesives, straps, or other fasteners. For example, ridges or bumps or fabrics or other higher friction surfaces may be used. In still other implementations, the flexible frame 102 may be held within a skinfold using an adhesive or hook and loop fastener. In some implementations, these attachment mechanisms may be noncompressive and therefore may be comfortable for the patient to wear. In some implementations, the hook or loop may be adhered to an outer edge of the skinfold, and the other of the hook or loop may be disposed on the opposing tissue facing surfaces 104a, 104b adjacent the external facing surface 108. Because the tissue retraction system 100 may be maintained on the patient without straps, ambulatory movement of the patient may be increased compared to prior systems.

The shape of the flexible frame 102 may allow tissue to be displaced from or off (out of contact with) the incision site, increasing the ability to heal without infection. Furthermore, where there is no adhesive, adjustment of the tissue retraction system 100 on a patient is simple and easy. It may be adjusted quickly and easily or may be removed entirely when access is needed to the incision. Furthermore, the lack of adhesive reduces the chance of trauma or damage to skin or other skin integrity challenges.

In some implementations, the flexible frame 102 may be formed of a moderately compressible material of a suitable durometer so that the patient movement causes a bellow effect. Such a compressible bellow effect may allow exchange of air inside the skinfold. This may maximize passive air exchange with ambient air outside of the skinfold. In these implementations, movement of the patient, such as rolling over in bed or moving about a healthcare facility may result in cyclic compression of the flexible frame 102, causing the flexible frame 102 to act as a bellows, drawing in and pushing out air. As the air comes in contact with the skin of the skinfold, increased evaporation and dissipation of heat may occur. Accordingly, in some implementations the flexible frame may be structurally arranged to compress in a lateral direction (e.g., compressing the tissue facing surfaces 104a and 104b toward each other) within designed criteria to permit sufficient bellow effect as described herein. For example, in some implementations the flexible frame is sized and arranged to permit lateral compression of between about 10% and 50% of the uncompressed size under a load of 20 lbs. In one non-limiting example, the uncompressed width 126 (FIG. 1C) of the external facing surface 108 is about 5 inches, and under a lateral load of about 20 lbs, the flexible frame compresses between about 0.5 and 2.5 inches. In other implementations, the flexible frame is sized and arranged to permit lateral compression of between about 10% and 30% of the uncompressed size under load of about 20 lbs. Other ranges are also contemplated.

Figure 4A:
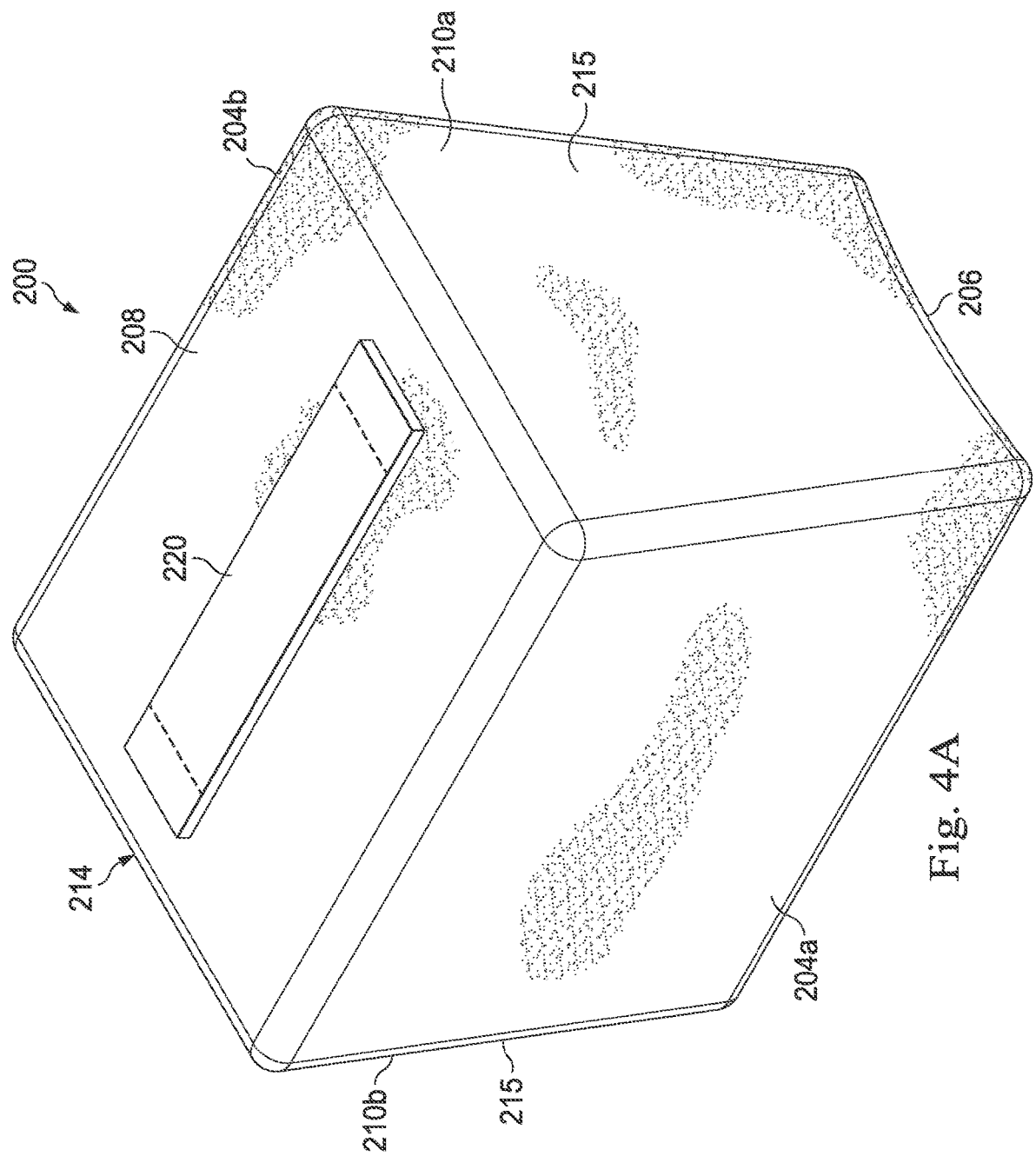
FIG. 4A is an illustration of a perspective view of another exemplary tissue retraction system according to an exemplary implementation of the present disclosure.

FIGS. 4A, 4B, and 4C show a tissue retraction system 200 formed of an individual support body segment 214. The support body segment 214 may be sized and shaped like the support body segments 114 described herein, but may be configured for individual placement and support within a fold of tissue on the patient. Accordingly, the support body segment 214 may mimic the support body segments 114 described herein, and may include a tissue facing surface 204, an internal facing surface 206, an external facing surface 208, and edges or ends 215 that correspond to ends 210a, 210b. These correspond to the description of the tissue facing surface 104, the internal facing surface 106, the external facing surface 108, and the edges or ends 115 that correspond to the ends 110a, 110b. Accordingly, the description with respect to FIGS. 1A-1D apply to FIGS. 4A-4C. In this implementation, the support body segment 214 may also include a graspable handle 220. In the implementation shown, the handle 220 may be disposed on the external facing surface 208, while in other embodiments, the handle 220 may be otherwise formed on the support body segment 214. In some implementations, the handle 220 is molded or formed into a portion of the support body segment 214. In other implementations, the handle 220 is adhered using an adhesive. In some implementations, the handle 220 may project outwardly from the surface 208 as a graspable knob, while in other implementations, the handle may be a projecting loop structure. Yet other handles are formed into and below the surface of the external facing surface 208.

Figure 5:
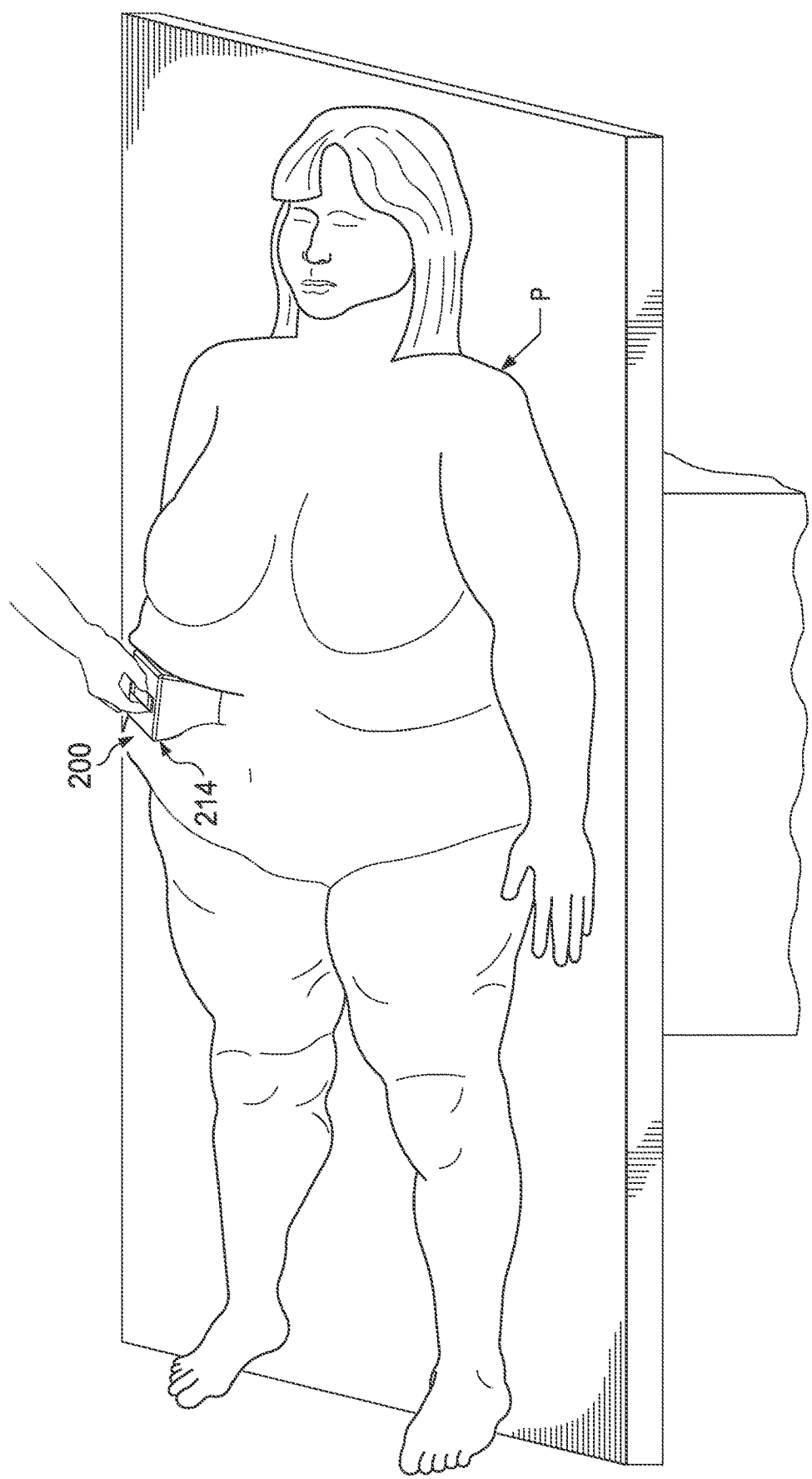
FIG. 5 is an illustration of a patient with the tissue retraction system disposed within a fold of adipose tissue according to an exemplary implementation of the present disclosure.

FIG. 5 shows the tissue retraction system 200 in use on a patient P. Because of its size, the tissue retraction system 200 may be disposed within a fold of skin on the patient in a much smaller region. Although only one tissue retraction system 200 is shown in FIG. 5, in use, multiple tissue retraction systems 200 may be used simultaneously on the single patient. For example, a user or patient may apply a first tissue retraction system 200 on one side of an incision, and a second tissue retraction system 200 on another side of the incision. Accordingly, the tissue retraction systems 200 may be spaced apart from each other providing access to the incision while maintaining separation of the skinfold. In yet other implementations, a first tissue retraction system 200 may be placed directly adjacent to a second tissue retraction system 200. Other implementations and use scenarios are also contemplated.

Figure 6A:
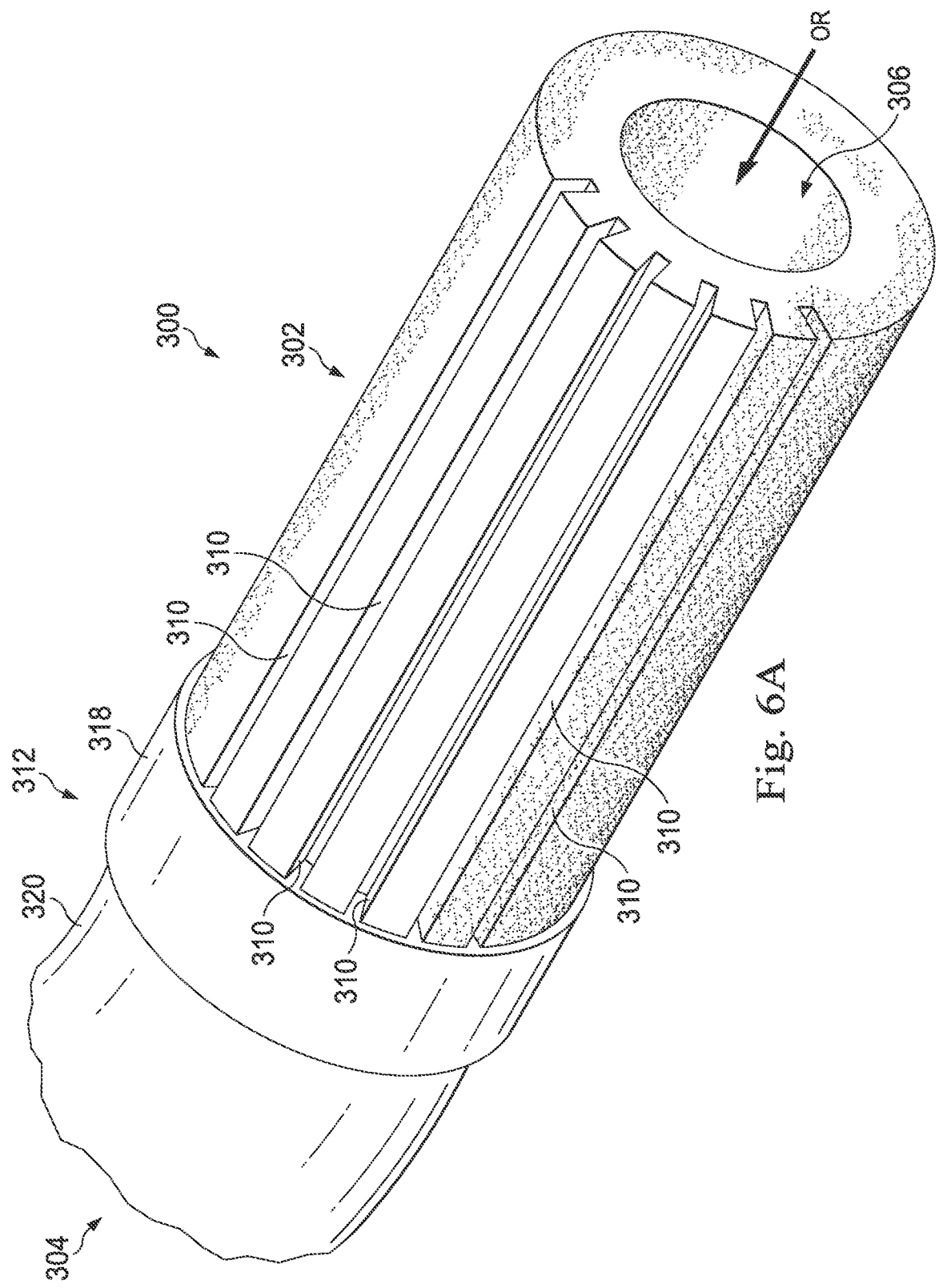
FIG. 6A is an illustration of a perspective view of yet another exemplary tissue retraction system according to an exemplary implementation of the present disclosure.
Figure 6B:
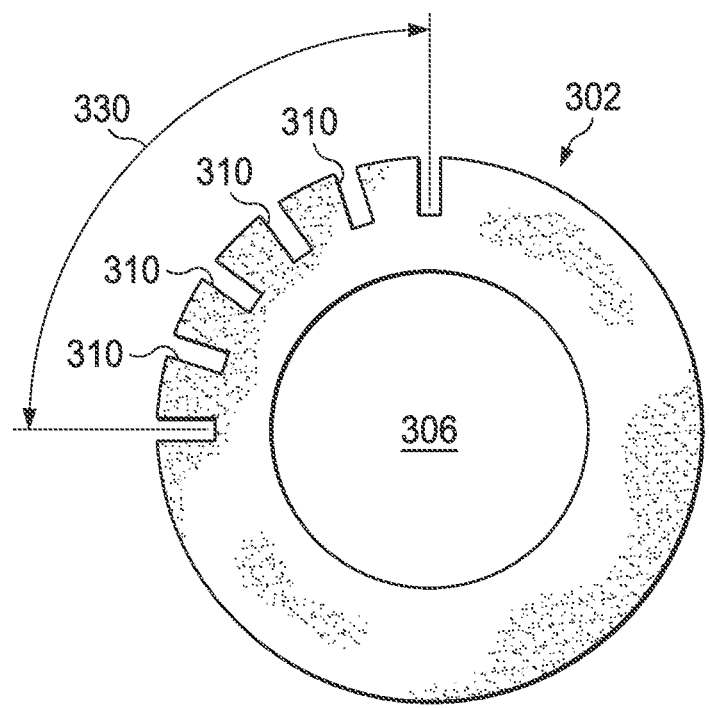
FIG. 6B is an illustration of an end view of the exemplary tissue retraction system of FIG. 6A according to an exemplary implementation.
Figure 6E:
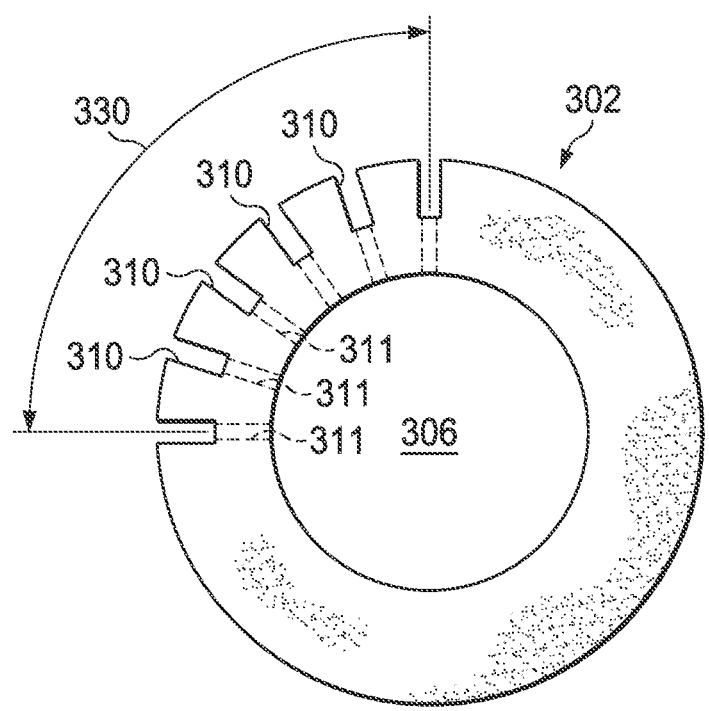
FIG. 6E is an illustration of an end view of the exemplary tissue retraction system of FIG. 6D taken through lines 6E-6E according to an exemplary implementation.
Figure 6C:
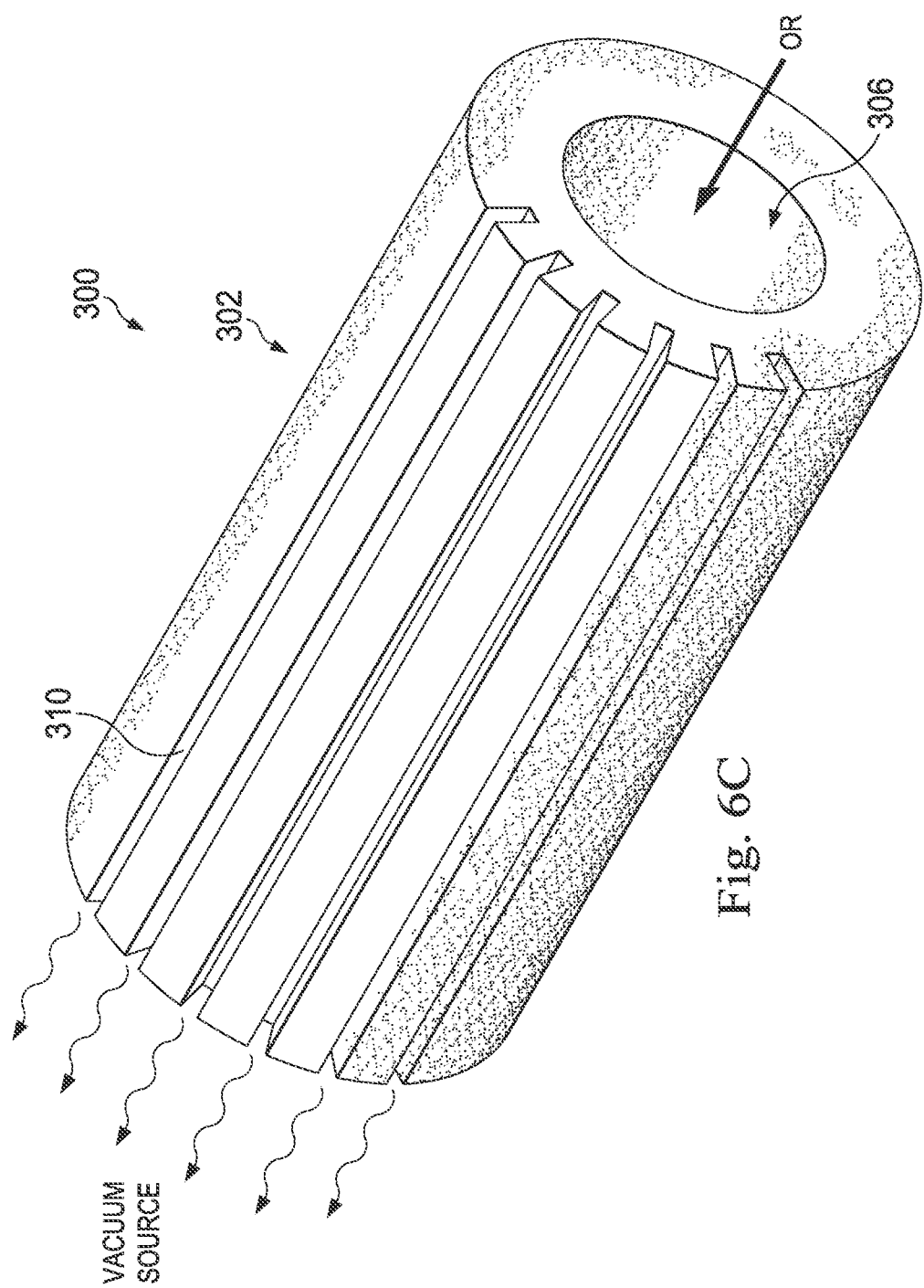
FIG. 6C is an illustration of a perspective view of a flexible frame of the exemplary tissue retraction system of FIG. 6A according to an exemplary implementation.

FIGS. 6A, 6B, and 6C show a tissue retraction system 300 that includes a flexible frame 302 and an active aeration system 304. The flexible frame 302 in this embodiment is selectively shaped and formed to structurally separate a fold of skin and is formed to compress and expand within the skinfold under load while the patient moves. In this embodiment, flexible frame 302 is of generally cylindrical shape having a substantially circular cross-section, such that the tissue facing surfaces, the internal facing surface, and the external facing surface are defined by respective curved portions of the circumference of flexible frame 302. In some embodiments, flexible frame 302 may have other suitable cross-sections, such as elliptical wherein the tissue facing surfaces are defined by the longer curvilinear surfaces of the elliptical configuration. The flexible frame 302 may be formed of any material sufficient to provide some amount of flexibility for comfort and form and that may allow the flexible frame 302 to bend and conform to the shape of the patient.

The flexible frame 302 may include an internal cavity 306. The cavity 306 may be hollow in some implementations accordingly, while in other implementations, the cavity 306 may contain a core. For example, the core may be formed of an absorbent material to absorb sweat and reduce the moisture level within the skinfold.

The active aeration system 304 in this implementation includes a plurality of aeration lines or channels 310 (of flutes) and an air-flow generator 312. In the example shown in FIGS. 6B and 6C, the aeration channels 310 are external channels formed into and axially along an outer surface of the flexible frame 302 and are sized and arranged to accommodate the passage of air therethrough. In such examples, channels 310 are open at the outer surface of flexible frame 302 and do not extend into the cavity 306. In some implementations, the aeration channels 310 are internal aeration lines, formed along an inner wall of the flexible frame 302 or otherwise providing air circulation between the folds of tissue. In some instances, aeration channels 310 further provide increased surface area to enhance heat transfer capability. For example, the outer surface may include lines, channels, grooves, valleys, or texturing to increase the emissivity of the device to improve heat transfer from the person's skin, via radiation or conduction, reducing the temperature between skin folds which may result in less perspiration and dryer environment.

As the embodiment shown in FIG. 6B, the aeration channels 310 extend radially across an arc that extends, in this embodiment, less than 180° about the circumference of the outer surface of the flexible frame 302. In other embodiments, the aeration channels 310 are within a smaller arc. In this implementation, the aeration channels extend along and form an arc 330 of about 90° about the circumference of the outer surface of the flexible frame. However, other implementations have aeration channels that form an arc 330 of about 60°. In some implementations the arc 330 may be in a range of about 45-120 degrees. However, the aeration channels 310 may extend across any range that will provide cooling aeration within a skinfold and may be included in those portions of the outer surface of flexible frame 302 that define one or both of the first and second tissue facing surfaces or the internal facing surface. The example shown includes six aeration channels 310, however other embodiments may have more or fewer aeration channels 310. As will be described below, the aeration channels 310 may accommodate airflow forced to move along the outer surface of the flexible frame 302, to provide cooling and evaporation of sweat to reduce the moisture level within the fold. Thus, wounds may heal more quickly, with a reduced chance of infection because the environment may stay drier and cooler than without a tissue retraction system.

The airflow generator 312 in this implementation is a sleeve 318 as shown in FIG. 6A that extends about an end of the flexible frame 302 and a hose 320 attached to the sleeve 318. The hose 320 in some embodiments, may be a vacuum hose attachable to a vacuum system within a treatment area, such as within a surgery room or other health care room within a healthcare facility. In other embodiments, the hose 320 may be a compressed air hose that provides compressed air to the flexible frame 302. The sleeve 318 may be shaped to provide positive pressure airflow or negative pressure airflow only to the aeration channels 310. In other embodiments, the sleeve 318 may be shaped to provide positive pressure airflow or negative pressure airflow to the aeration channels 310 and the internal cavity of the flexible frame 302.

Figure 6D:
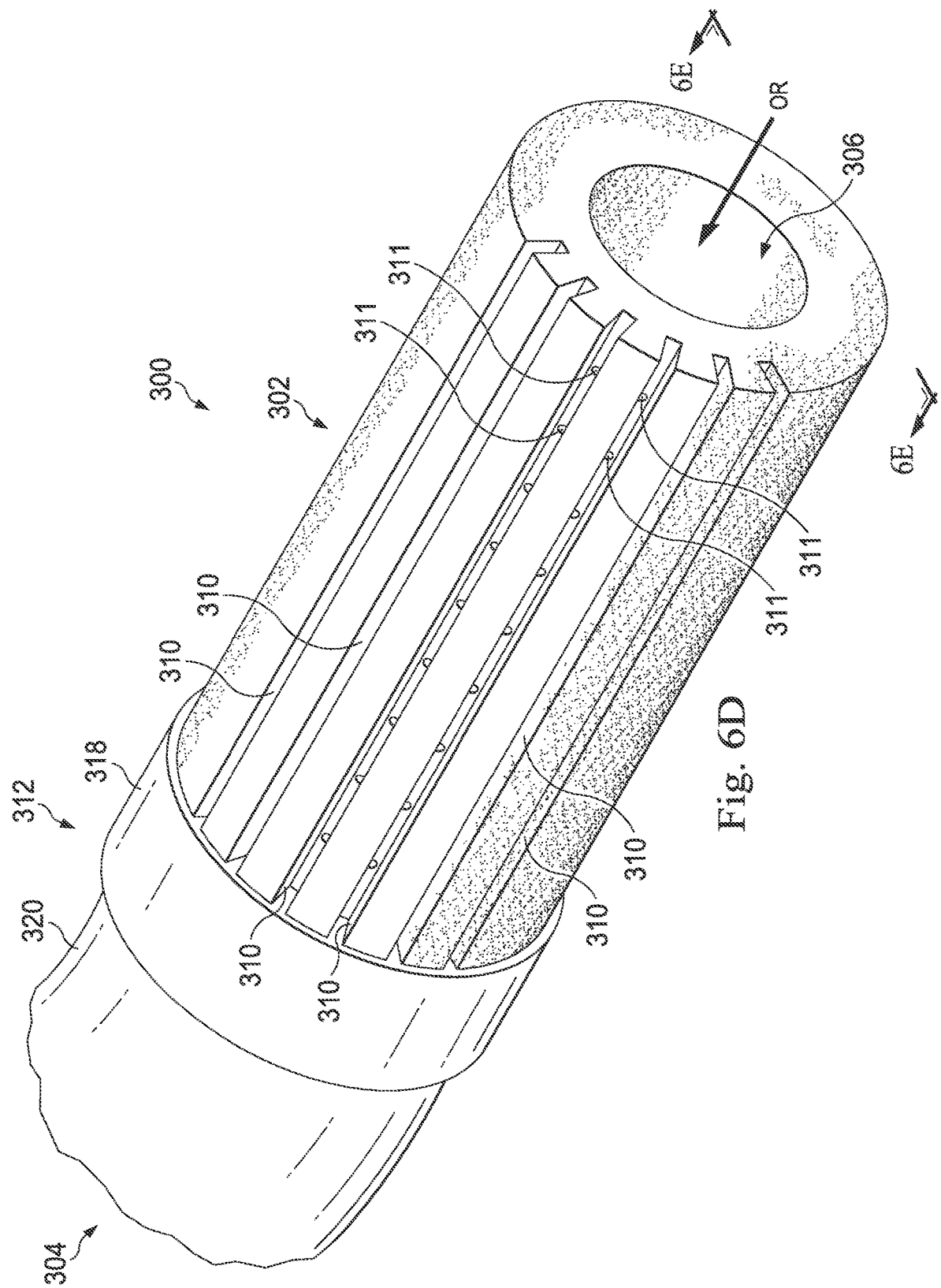
FIG. 6D is an illustration of a perspective view of a further exemplary tissue retraction system according to an exemplary implementation of the present disclosure.
Figure 7C:
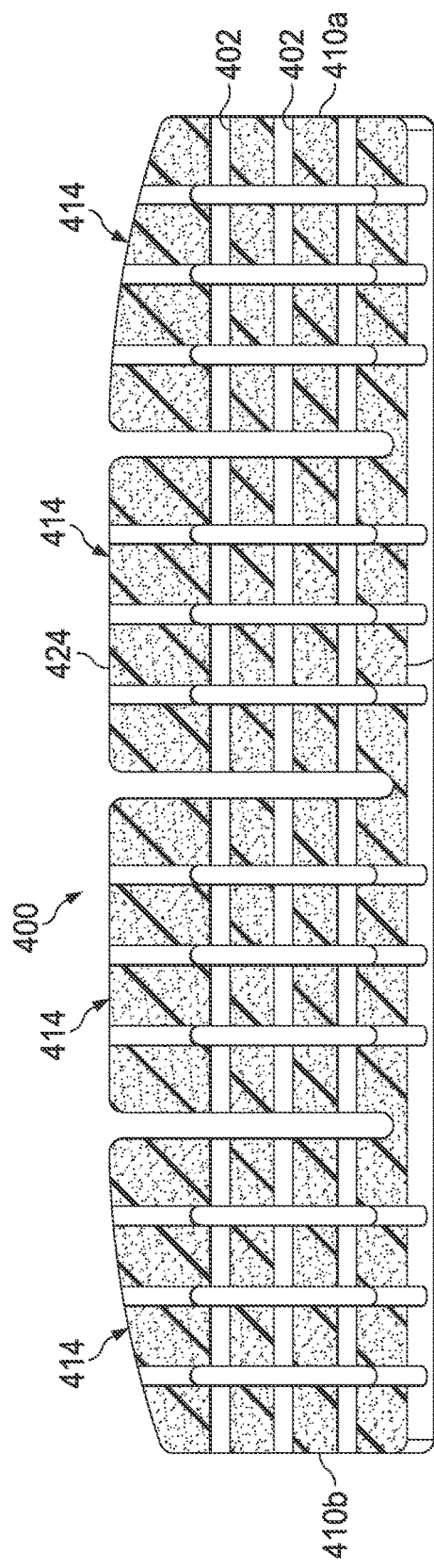
FIG. 7C is an illustration of a cross-sectional view of the exemplary tissue retraction system of FIG. 7B taken through lines 7C-7C according to an exemplary implementation.
Figure 7D:
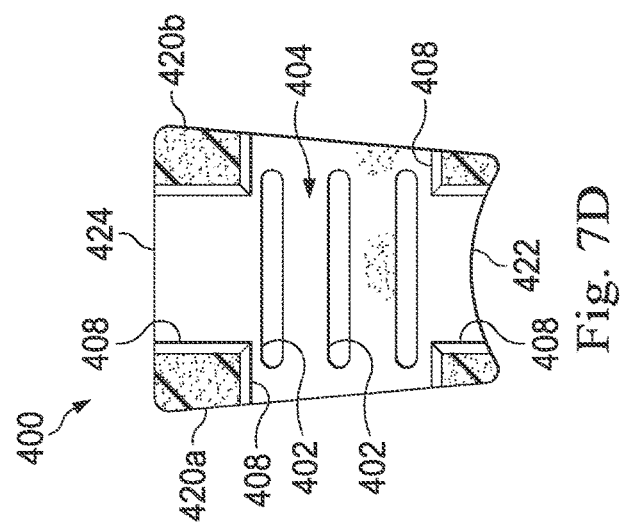
FIG. 7D is an illustration of a cross-sectional view of the exemplary tissue retraction system of FIG. 7A taken through lines 7D-7D according to an exemplary implementation.

FIGS. 6D and 6E show a variation of the tissue retraction system 300 illustrated in FIGS. 6A, 6B, and 6C that includes additional or alternative airflow features that direct airflow into or out of the skinfold. In this variation, one or more holes 311 are formed to extend along the length of flexible frame 302 from the proximal end to the distal end. Holes 311 may extend through flexible frame 302 into the inner cavity 306 (or lumen) thereby defining a fluid passage between the exterior of the flexible frame 302 to the interior cavity 306. In the implementation shown, the holes 311 are formed within the channels 310. Such holes 311 facilitate the movement and exchange of air within the skinfold of the patient, allowing for a reduction in moisture and/or heat. When used with an application of positive pressure, for example, air would be pushed through the cavity 306 and exit through holes 311, exchanging the air within the skinfold, which is conducive to drying the skin. As such, with this variation of tissue retraction system 300, intra-fold air exchange (air exchange within the skinfold) is amplified in the presence of positive pressure, or negative pressure, connected to one end of flexible frame 302. In some arrangements, holes 311 may be aligned with channels 310. In other arrangements, holes 311 may be disposed between channels 310. In yet further arrangements, holes 311 may be provided without channels 310.

FIGS. 7A, 7B, 7C, and 7D show a tissue retraction system 400 that includes a flexible frame 401. Many of the features of the tissue retraction system 400 are like those described above with reference to the tissue retraction system 100 and will not be repeated here. The retraction system 400 however, includes one or more apertures 402 and a hollow core or cavity 404 that may promote additional airflow or air volume within a skinfold when worn by the patient. Similar to the tissue retraction system 100, the tissue retraction system 400 includes support body segments 414, tissue facing surfaces 420a and 420b, internal facing surface 422, and external facing surface 424. As can be seen, the flexible frame 402 also includes ends 410a and 410b.

In this implementation, each of the support body segments 414 includes three apertures 402, which in this example, are formed as extended slots 408 that may provide additional aeration. In some embodiments, the slots 408 are open and provide airflow, while in other embodiments, the slots 408 contain absorbent material that may wick sweat or otherwise absorb sweat from the skin fold. In the implementation shown, the apertures 402, shown as the slots 408 are formed on all external sides of the flexible frame 402. Accordingly, the apertures 402 shown as the slots 408 are formed in the internal facing surface 422, and the tissue facing surface 420a, 420b, and in the external facing surface 424. In some implementations, the apertures 402 are centrally disposed in any particular sidewall to provide central aeration. However, in other embodiments, the apertures 402 are offset toward one side or another to provide a varying amount of variation to particular areas within the fold. For example, in some implementations, the apertures formed in the internal facing surface 422 are larger than the apertures formed in the tissue facing surfaces 420a and 420b. In some implementations, the hollow core or cavity 404 is formed as a longitudinally extending slot extending from one end 410a to the other end 410b of the flexible frame 401. The flexible frame 41 may have the structural features described herein, including the ability to act as a bellows to drive airflow through the apertures 402 to provide cooling and fresh air to tissue within the skinfold of a patient.

Figure 8B:
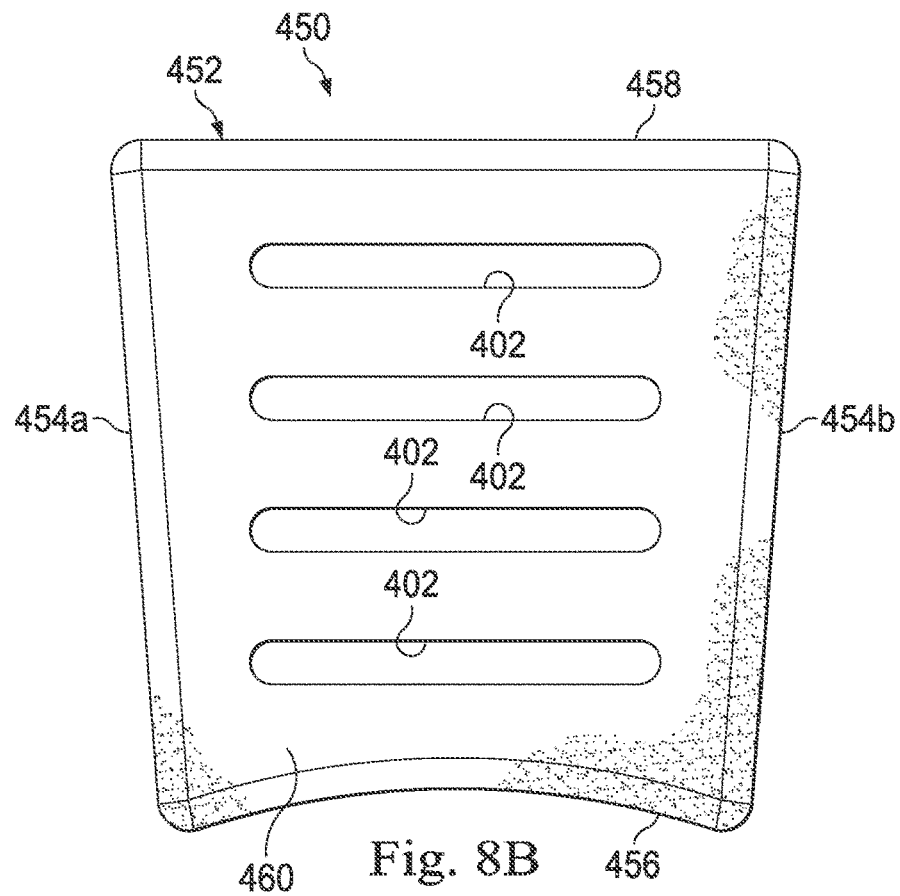
FIG. 8B is an illustration of a side view of the exemplary tissue retraction system of FIG. 8A according to an exemplary implementation.

FIGS. 8A and 8B show a single support body segment 452 that by itself or together with additional support body segments 452 form a tissue retraction system 450. Like other support body segments described herein, this support body segment 452 includes tissue facing surfaces 454 and 454b, an internal facing surface 456, and an external facing surface 458. As can be seen here, the apertures 402 may be formed on all six sides of the support body segment 452, or alternatively, on fewer than six sides of the support body segment 452. In some implementations, the apertures 402 are not being disposed on the side surfaces 454a and 454b (as shown). Thus, in this implementation, the side surfaces 454a and 454b are devoid of apertures 402. In other implementations, other surfaces are devoid of the apertures 402. In some implementations, the apertures 402 are formed on the internal facing surface 456 and the external facing surface 458, and end surfaces 460. In the implementation of FIGS. 8A and 8B, the side surfaces include four apertures. It should be apparent that any number of apertures may be included on any particular side. It is worth noting that the described handle may be included on any embodiment or implementation described herein.

In some implementations, a separate removable sleeve may be disposed over the flexible frame 102. The removable sleeve may be formed of an absorbent material, to help absorb sweat and reduce the level of humidity within the skinfold. When needed or desired, the removable sleeve may be removed from the flexible frame 102 and replaced with a new removable sleeve. Accordingly, this may keep the area near an incision within a skinfold relatively clean with fresh removable sleeves. In such embodiments, the flexible frame may be reusable. Accordingly, it may be nonporous while the removable sleeve may be absorbent.

Figure 9A:
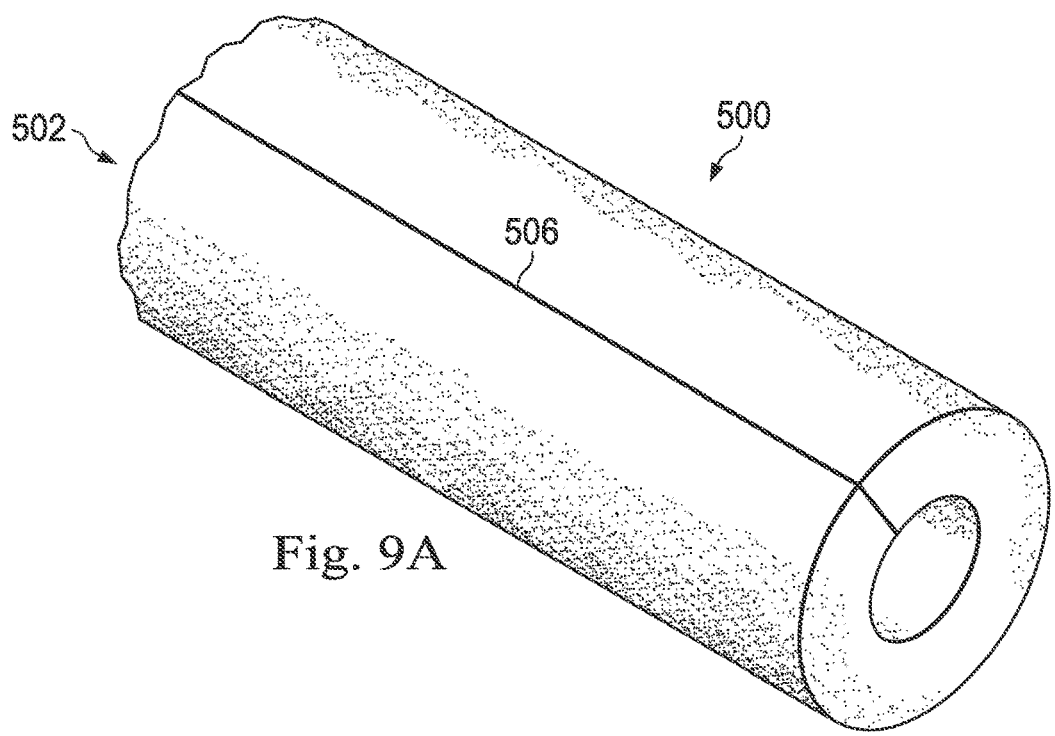
FIG. 9A illustrates a flexible frame of an exemplary tissue retraction system according to an exemplary implementation of the present disclosure.
Figure 9B:
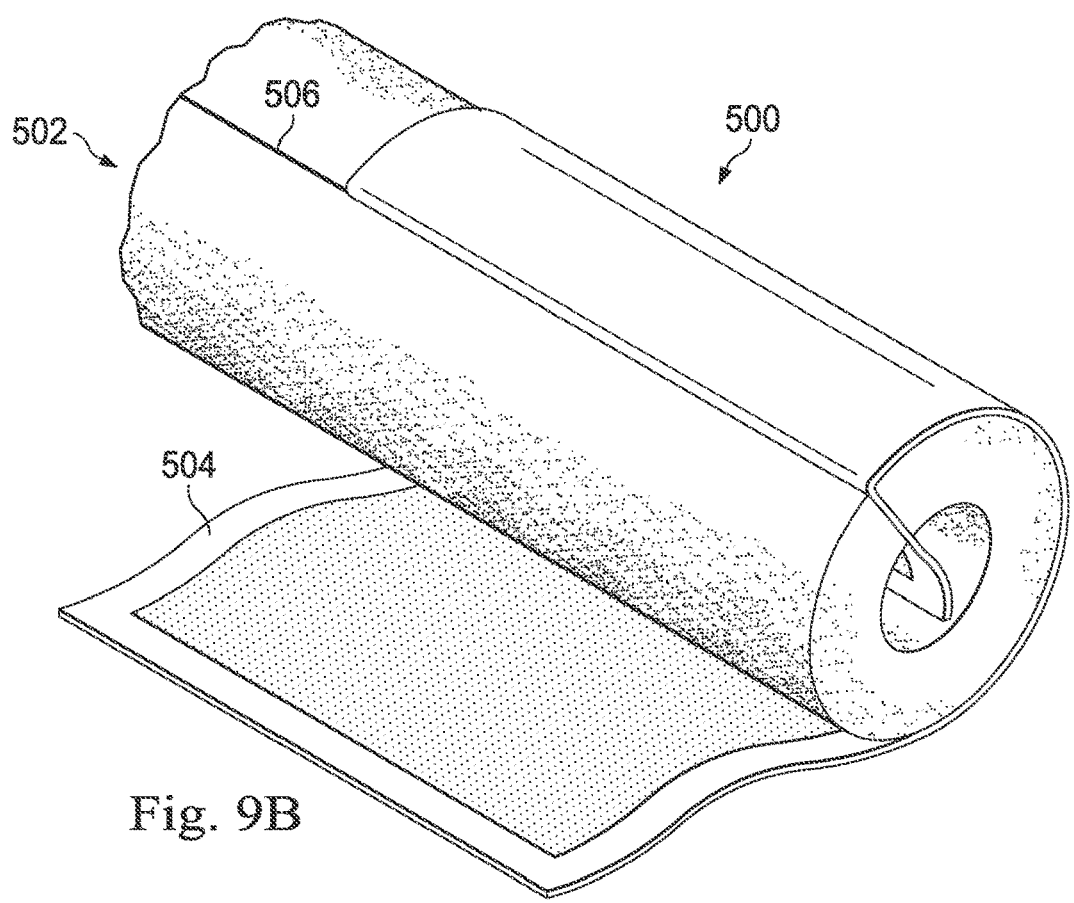
FIG. 9B illustrates an absorbable sleeve partially applied to the flexible frame of the exemplary tissue retraction system according to an exemplary implementation.
Figure 9C:
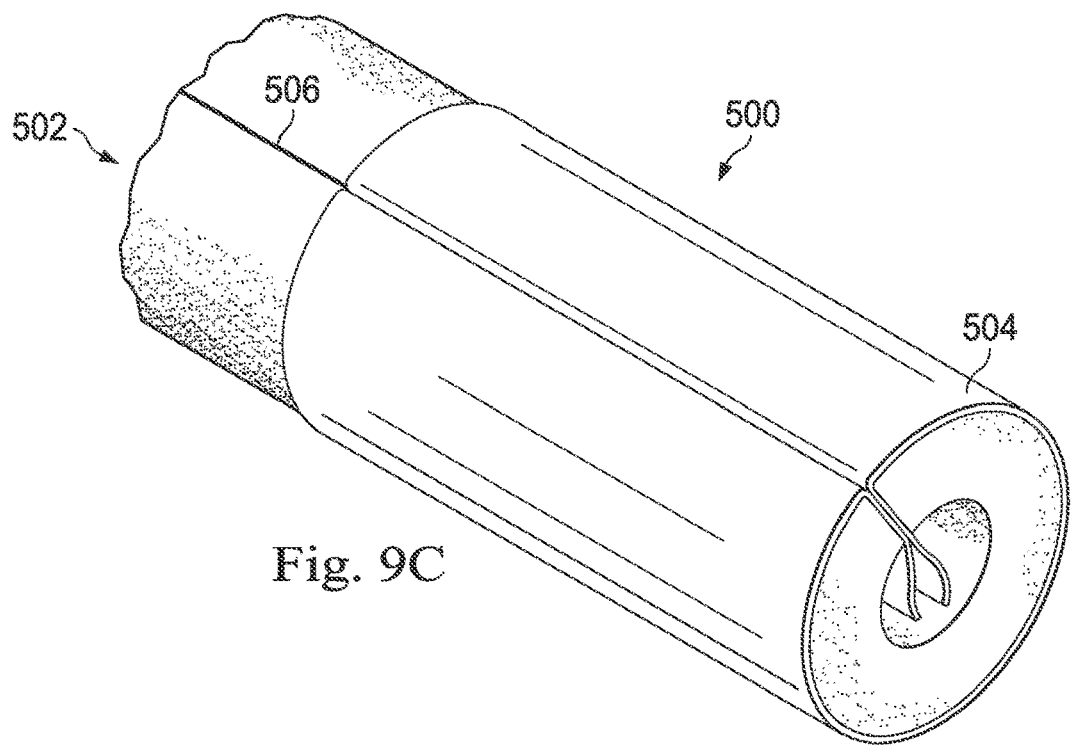
FIG. 9C illustrates an absorbable sleeve applied to the flexible frame of the exemplary tissue retraction system according to an exemplary implementation.
Figure 9D:
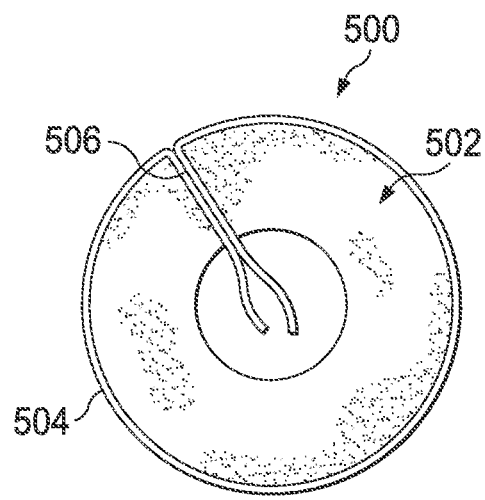
FIG. 9D illustrates an end view of tissue retraction system according to an exemplary implementation.

FIGS. 9A, 9B, 9C, and 9D show a tissue retraction system 500 with a removable, absorbent sleeve disposed thereon. The tissue retraction system 500 includes a flexible frame 502 and a removable absorbable sleeve 504. In this implementation, the flexible frame 502 has a slit 506 formed therein to receive ends of the removable absorbent sleeve 504. The flexible frame in this implementation is cylindrically shaped and has a hollow core. Some sleeve embodiments may include apertures as described with reference to FIGS. 7A, 7B, 7C, and 7D. Accordingly, the removable absorbent sleeve 504 is a replaceable sleeve that may be maintained on the flexible frame 102 without requiring additional adhesive. Thus, the removable absorbent sleeve 504 may be easily removed for disposal, and a new replaceable sleeve may be easily disposed thereon by wrapping the flexible frame 502 and disposing the edges of the replaceable sleeve within the slit. It is worth noting that the replaceable sleeve 504 may be disposed on any of the frame embodiments described herein. In the embodiment shown, the removable, absorbent sleeve 504 is formed of a sheet of absorbent material wrapped to form a sleeve. In other implementations, the absorbent sleeve 504 is formed as sock-like sleeve that may be introduced over an end of the frame 502. The absorbent sleeve 504 may then be slid along the at least a portion of the length of the frame 502. In some implementations, the absorbent sleeve 504 extends only along a portion of the frame 502 as shown in FIGS. 9B and 9C. In other implementations, the absorbent sleeve 504 extends along substantially the entire length of the frame 502. In some implementations, an absorbent sleeve 504 is provided for each individual support body segment, and in other embodiments, a single absorbent sleeve 504 may extend over more than one individual support body segment. It is worth noting the slit may be formed in any of the embodiments described herein and the sleeve or sheets may be introduced in the slit to maintain an absorption material in place. Other systems for maintaining an absorption sheet or sleeve in place are contemplated, including simply wrapping the frame, using adhesives, using hook and loop fasteners, ties, or other methods.

Some tissue retraction systems described herein include for example, features and structure that enable the tissue retraction system to use compression (weight) of an adjacent skin fold to hold the abdominal retraction device in place; permit ambulatory movement of a person; not require the use of adhesive or appendages to keep the device in place; placed or reside "within" the pannus, while maintaining separation of a skin fold; allows for contact with and exchange of air to intra-fold skin; lift tissue off the incision site; be quickly and easily adjusted in the absence of adhesive; reduces a chance of skin integrity problems due to the lack of an adhesive.

Depending on the implementation, the tissue retraction system may be: constructed of closed cell polyethylene or other appropriate material, such as open cell and closed cell foam, polyethylene, cross-linked polyethylene, polyurethane, reticulated polyurethane, plastic, cardboard, or other biocompatible or appropriate material; exclusively constructed of super-absorbent material; flexible or compressible; generally elongated; substantially continuous; made be disposable or re-usable; may be air-permeable (either by cut-outs or porosity); may be reusable if the outer product skin is non-porous. In some implementations, if super-absorbent or absorbent materials are utilized on a reusable device, the super-absorbent or absorbent materials may be disposable.

In some implementations, the tissue retraction system may: maintain separation of skin fold; include serrations or clefts to help device flex or bend to conform to a radius of pannus and allows product to ship in a straight condition; be formed of or may include a covering including fungicidal and bactericidal additives; be vapor permeable, perforated, or have voids to allow exposure of skin to ambient air outside of skin fold for increased aeration or evaporation of sweat or dissipation of heat (which may prevent sweat from occurring in first place); be compressible material of suitable durometer so patient movement causes billow effect of wedge, allowing exchange of air inside skin-fold; maximize passive air exchange with ambient air outside of skin fold.

In some implementations, the tissue retraction system may: be manufactured by thermoforming, layering, additive manufacturing, or subtractive manufacturing. Accordingly, the tissue retraction system may include integration of super-absorbent material. Super-absorbent materials in some implementations may be in the form of a sleeve that acts as disposable outer covering to absorb sweat. In some implementations, the absorbable sleeve may absorb about approximately 8 ounces (using Tranquility Thinliner Moisture Management), although the materials may be varied to absorb any target absorption level. In some implementations, the tissue retraction system is shaped as a wedge, and the wedge may have a slit so sheets or a sleeve may attach to the wedge. In some implementations, the core may be filled with super-absorbent material to absorb sweat through vapor permeable wedge or wedge made of superabsorbent.

In some implementations, the tissue retraction system may: be integrated with vacuum from vacuum source. The tissue retraction system may have flutes, ridges or channels so vacuum can pull air around an exterior of the tissue retraction system as opposed to through air-permeable substrate. This may increase rate of evaporation and may increase air exchange, which may lower skin-fold temperature. In some implementations, the tissue retraction system may comprise a silver ion coating. In some implementations, the tissue retraction system may comprise tear-away, breakaway sections so wedge can be torn to length.

Figure 10:
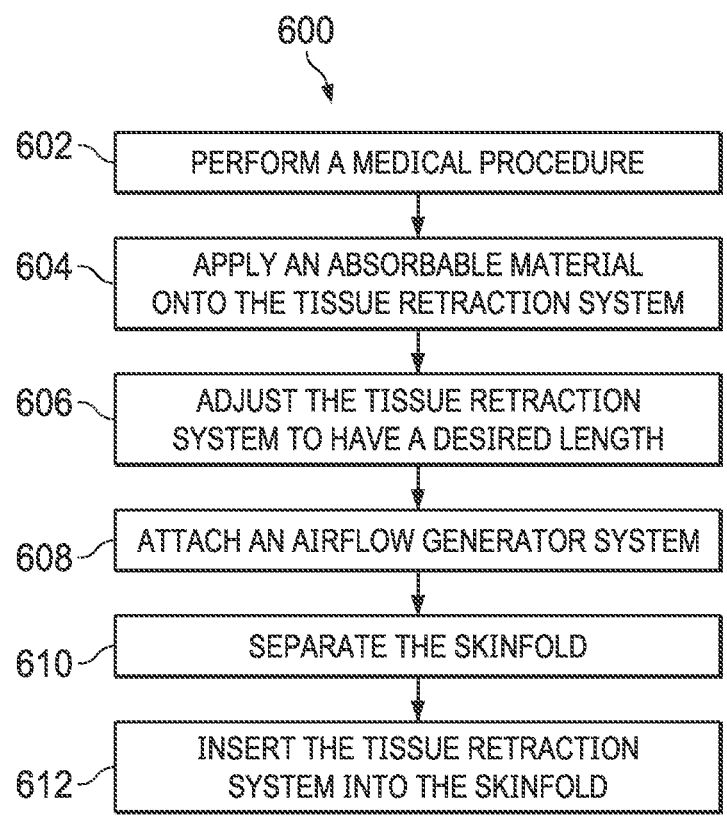
FIG. 10 is a flow chart illustrating a method of using a tissue retraction system according to an exemplary implementation of the present disclosure.

FIG. 10 is a flowchart illustrating an exemplary method 600 of preparing and using a tissue retraction system as disclosed herein. The method may begin at 602 by performing a medical procedure in an area within a skinfold. The procedure may be performed in a manner known in the art. In some implementations, the procedure may be a cesarean section to deliver a baby. After completing the procedure, whether it included sutures or other treatment, a tissue retraction system in accordance with any of the embodiments described herein, such as retraction system 100, may be prepared and introduced in a fold between pannus tissue to provide support and aeration to the treatment area. It is worth noting in some implementations, the tissue retraction system 100 may be used prior to a procedure in order to provide air that allows the area of the procedure to dry or otherwise assist with procedure cleanliness. In other implementations, the tissue retraction system is introduced prior to a medical procedure. It may be introduced to help dry and prepare the skin fold for a procedure. In some implementations, it is utilized without a procedure to provide aeration and relief to skin subject to rash, irritation, or other condition, in which cases the step of performing a medical procedure may not be performed.

The healthcare provider may prepare the tissue retraction system for placement in a skinfold of the patient. Depending on the implementation, preparing the tissue retraction system for use may include applying an absorbable material onto a flexible frame at 604. This absorbable material may be in the form of a sleeve, a sheet wrapped around the flexible frame to form a sleeve, a plug insertable into a hollow cavity or aperture of the tissue retraction system, or the absorbable material may take yet other forms. As described herein, the absorbable material may be a cotton material, napkin, sponge, anhydrous calcium chloride, soda lime, allochroic silica gel, activated carbon, or other absorbing material. At 606, the healthcare provider may also adjust the tissue retraction system to have a desired length by cutting or tearing the flexible frame. In some implementations, this may occur prior to applying the absorbable sleeve. In some implementations, preparing the tissue retraction system may include attaching it to an airflow generator system at 608 that may be a positive pressure or a negative pressure system that would promote air flow inside or outside the tissue retraction system. At 610, the healthcare provider may separate the skinfold of a patient and at 612, may take the flexible frame and introduce it between the skinfold on the patient. In some implementations, attachment to an airflow generator system may occur after introducing the tissue retraction system to the patient. In some implementations, the healthcare provider may use multiple independent rigid body supports or body segments and introduce one or more into the skin fold.

Depending on the implementation, care may be taken during placement of the flexible frame 102 into the fold to ensure that any active aeration system is properly positioned to provide the desired airflow and heat dissipation to the proper area of the patient. In some implementations, a positive pressure or negative pressure airflow system may be connected to the flexible frame 102, and if required, power to provide air flow to the flexible frame 102. As described herein, the tissue retraction system 100 may be removed as desired by the healthcare provider and any absorbent portions of the tissue retraction system may be replaced.

Figure 11:
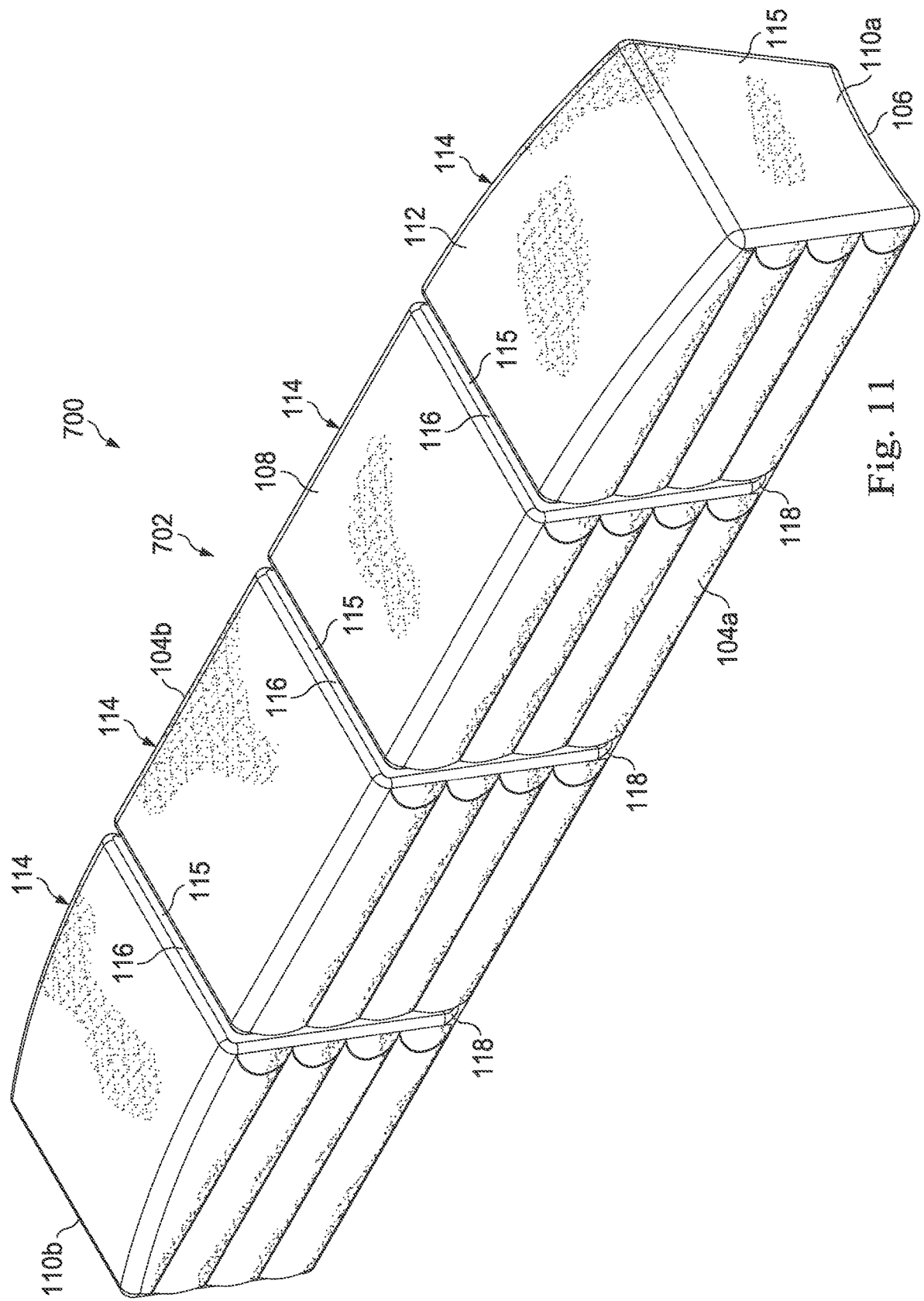
FIG. 11 is an illustration of a perspective view of an exemplary tissue retraction system according to an exemplary implementation of the present disclosure.

FIG. 11 shows another embodiment similar in some respects to the device shown in FIGS. 1A-1D. In this embodiment, referenced herein by the numeral 700, the device includes a frame 702 having ripples or a series of protruding portions along the lateral sides that interface with the patient's skin. These protruding portions may be formed in rows as shown or may be otherwise arranged. These side features may help provide additional aeration between the skin and the device itself, providing additional comfort to the patient. Other embodiments include dimpled protrusions or other shapes.

Although described for use in a medical procedure, the methods and systems described herein may also be used outside the hospital environment and in a home or other environment. For example, a user may utilize the systems herein at home to separate and displace tissue when tissue has a rash or is otherwise irritated. Other home-uses are also contemplated.

While providing many advantages over known systems, the tissue retraction system disclosed herein is particularly useful on obese patients because it may be effectively used without wrapping around a portion of the patient. For example, it may be entirely applied and used without lifting of limbs, the head, the torso, or legs. It can be applied and used entirely from one side of the patient, such as the patient's front side or the patient's back side. Other advantages, benefits, and uses are described in U.S. Pat. No. 9,408,741, incorporated herein by reference in its entirety.

Applicants note that the procedures disclosed herein are merely exemplary and that the systems and method disclosed herein may be utilized for various other medical processes and procedures. Although several selected implementations have been illustrated and described in detail, it will be understood that they are exemplary, and that a variety of substitutions and alterations are possible without departing from the spirit and scope of the present invention, as defined by the following claims.

We claim:

1. A system for absorbing sweat from within a skinfold of a patient, comprising:
   an elongate frame having an exterior surface and a central hollow core extending therethrough, a non-secured slit extending through said exterior surface and into and communicating with said central hollow core, said slit extending at least for an axial length along said elongate frame, said slit being accessible and configured for receipt of an edge of a sheet of sweat absorbent material disposed within the skinfold of said patient and for maintaining said elongate frame and said sheet in place.

2. A system according to claim 1, wherein said elongate frame is cylindrical.

3. A system according to claim 2, wherein said central hollow core is cylindrical.

4. A system according to claim 3, wherein said slit extends substantially along an entire length of said elongate frame.

5. A system according to claim 1, further comprising a sheet of absorbent material having a thickness dimensioned for receipt into said slit of said elongate frame.

6. A system according to claim 5, wherein the said sheet of absorbent material is attached to said elongate frame.

7. A system for absorbing sweat from within a skinfold of a patient, comprising:
an elongate frame having an exterior surface and a central hollow core extending therethrough, a slit extending through said exterior surface and into and communicating with said central hollow core, said slit extending at least for an axial length along said elongate frame; and
a sheet of absorbent material attached to said frame, a portion of said sheet being sized and configured for receipt within said skinfold of said patient, said sheet of absorbent material including an edge, said edge extending through said slit and into said central hollow core, thereby attaching said sheet and said elongate frame.

8. A system according to claim 7, wherein said absorbent material is selected from the group of materials consisting of vapor permeable, perforated, or containing voids that allow exposure of skin to ambient air outside of the skinfold.

9. A system according to claim 7, wherein said absorbent material includes copper, silver, or antimicrobial substance therein.

10. A system according to claim 7, wherein another portion of said sheet extends around a portion of said exterior surface of said elongate frame.

11. A system according to claim 10, wherein said elongate frame is cylindrical and said another sheet portion around said exterior surface of said elongate frame defines a sleeve.

12. A system according to claim 11, wherein said elongate frame with said sleeve thereon are dimensioned and configured to fit within the skinfold of a patient.

13. A system according to claim 7, wherein said elongate frame is configured to be integrated with a vacuum source.

14. A system for absorbing sweat from within a skinfold of a patient, comprising:
a flexible frame having an exterior surface and a cavity extending therethrough, at least one aperture extending through said exterior surface and into and communicating with said cavity; and
sweat absorbent material on said exterior surface of said flexible frame in communication with said at least one aperture, a portion of said sweat absorbent material being sized and configured to fit within and separate tissue of a skinfold of a pannus of said patient and to wick sweat or otherwise absorb sweat from the skinfold.

15. A system according to claim 14, wherein said at least one aperture is an elongate slot.

16. A system according to claim 14, wherein there are a plurality of apertures.

17. A system according to claim 14, wherein said flexible frame with said sweat absorbent material thereon is dimensioned and configured to fit within said skinfold of said pannus of said patient.

18. A system according to claim 14, wherein said flexible frame is configured to be integrated with a vacuum source.

19. A system according to claim 18, wherein said flexible frame has a plurality of apertures.

20. A system according to claim 18, wherein said flexible frame is elongate having opposite ends, and wherein said system further comprises a conduit attached to said flexible frame at one of said opposite ends, said conduit being integrated with said flexible frame and said vacuum source and in fluid communication with said cavity and said apertures.

21. A system according to claim 20, wherein said conduit is a vacuum hose attachable to said vacuum source.

22. A system according to claim 14, wherein said flexible frame is cylindrical.

23. A system for absorbing sweat from within a skinfold of a patient, comprising:
a rigid frame having a cavity and an attachment feature for attaching an absorbent material, said attachment feature communicating with said cavity;
sweat absorbent material attached to said frame by said attachment feature and in communication with said cavity, said sweat absorbent material being sized and configured for receipt within said skinfold; and
a conduit attached to said rigid frame and attachable to a vacuum source, said conduit being in fluid communication with said cavity through which sweat from said skinfold may pass.

24. A system according to claim 23, wherein a first portion of said sweat absorbent material extends into said cavity, and wherein a second portion of said sweat absorbent material is sized and configured for receipt within said skinfold.

25. A system according to claim 23, wherein said sweat absorbent material comprises a sheet having an edge, wherein said attachment feature is a slit extending through said rigid frame, and wherein said edge extends into said cavity through said slit.

26. A system according to claim 25, wherein said skinfold is a skinfold of a pannus of said patient, a portion of said sweat absorbent material being sized and configured to fit within said skinfold of said pannus of said patient.

27. A system according to claim 26, wherein said rigid frame with said sweat absorbent material is dimensioned and configured to fit within said skinfold of said pannus of said patient.

* * * * *